United States Patent
Kunz et al.

(10) Patent No.: US 10,583,625 B2
(45) Date of Patent: Mar. 10, 2020

(54) PLURALITY OF MASS-PRODUCED MULTI-COMPONENT PLASTIC HOUSINGS

(71) Applicant: Braun GmbH, Kronberg (DE)

(72) Inventors: Marc Kunz, Görgeshausen (DE); Werner Huebscher, Waldems Bermbach (DE); Kris Lueckel, Schwalbach (DE); Sven Schäfer, Hohenstein (DE); Stefan Gehard Triebig, Birkenfeld (DE)

(73) Assignee: BRAUN GMBH, Kronberg (DE)

( * ) Notice: Subject to any disclaimer, the term of this patent is extended or adjusted under 35 U.S.C. 154(b) by 697 days.

(21) Appl. No.: 14/755,277

(22) Filed: Jun. 30, 2015

(65) Prior Publication Data
US 2017/0001403 A1  Jan. 5, 2017

(51) Int. Cl.
*B32B 1/00* (2006.01)
*B32B 1/08* (2006.01)
(Continued)

(52) U.S. Cl.
CPC ............. *B32B 1/08* (2013.01); *A46B 13/02* (2013.01); *B25G 1/10* (2013.01); *B29C 45/1676* (2013.01);
(Continued)

(58) Field of Classification Search
CPC ....... B25G 1/10; B29C 45/1676; B29C 45/14; B29C 2045/1682; B32B 1/08;
(Continued)

(56) References Cited

U.S. PATENT DOCUMENTS

| | | |
|---|---|---|
| 3,374,304 A | 3/1968 | Ayres |
| 4,969,231 A | 11/1990 | Mader |
| (Continued) | | |

FOREIGN PATENT DOCUMENTS

| | | |
|---|---|---|
| DE | 4204621 | 8/1993 |
| DE | 10204806 | 8/2003 |
| (Continued) | | |

OTHER PUBLICATIONS

International Search Report with Written Opinion, dated Sep. 22, 2016, 16 pages.

*Primary Examiner* — Monica S Carter
*Assistant Examiner* — Katina N. Henson
(74) *Attorney, Agent, or Firm* — Vladimir Vitenberg

(57) ABSTRACT

A plurality of mass-produced multi-component housings having a length and comprising at least a first component comprising a first plastic material, a second component comprising a second plastic material, and a third component comprising a third plastic material. Each of the housings includes at least one tolerance-elimination element made of the second plastic material and longitudinally attached to the first component along the housing's longitudinal axis. The tolerance-elimination element has an average length extending parallel to the housing's longitudinal axis, which average length is at least ten times less than the length of the housing. The third component at least partially forms an outer surface of the housing, so that the tolerance-elimination element is at least partially overmolded by the third plastic material. The tolerance-elimination elements of the plurality of multi-component housings are structured to cause lengthwise maximal dimension variations of the length L among the individual multi-component housings to be not greater than 0.1 mm.

15 Claims, 14 Drawing Sheets

(51) Int. Cl.
  *B29C 45/16* (2006.01)
  *A46B 13/02* (2006.01)
  *B25G 1/10* (2006.01)
  *B32B 27/08* (2006.01)
  *B29L 31/42* (2006.01)
  *A61C 17/22* (2006.01)

(52) U.S. Cl.
  CPC ............ *B32B 27/08* (2013.01); *A61C 17/225* (2013.01); *B29C 2045/1682* (2013.01); *B29L 2031/425* (2013.01); *B32B 2250/24* (2013.01); *B32B 2439/00* (2013.01); *B32B 2597/00* (2013.01)

(58) Field of Classification Search
  CPC . B32B 27/08; B32B 2250/24; B32B 2439/00; B32B 2597/00; A46B 13/02; B29L 2031/425; A61C 17/225
  USPC ........................................................ 15/22.1
  See application file for complete search history.

(56) References Cited

U.S. PATENT DOCUMENTS

| | | | |
|---|---|---|---|
| 5,740,586 A | 4/1998 | Gomas | |
| 5,823,069 A | 10/1998 | Roark | |
| 5,922,250 A | 7/1999 | Ishikawa et al. | |
| 6,223,384 B1 | 5/2001 | Kuhlen | |
| 6,322,738 B1 | 11/2001 | Sicilia et al. | |
| 6,464,920 B1 | 10/2002 | Kraemer | |
| 6,558,599 B1 | 5/2003 | Bethune | |
| 6,763,747 B1 | 7/2004 | Gierer | |
| 2002/0185778 A1 | 12/2002 | Armbruster | |
| 2003/0037391 A1 | 2/2003 | Pfenniger | |
| 2004/0113312 A1 | 6/2004 | Strahler | |
| 2004/0227308 A1* | 11/2004 | Long ................... B23B 31/1207 279/62 |
| 2006/0112505 A1 | 6/2006 | Birk | |
| 2006/0151911 A1 | 7/2006 | Zollner | |
| 2006/0284336 A1 | 12/2006 | Cipkar | |
| 2008/0216258 A1 | 9/2008 | Kressner | |
| 2010/0092711 A1 | 4/2010 | Atance Orden et al. | |
| 2010/0237536 A1 | 9/2010 | Horinaka | |
| 2011/0162155 A1 | 7/2011 | Wai | |
| 2012/0328814 A1 | 12/2012 | Atance Orden et al. | |
| 2017/0001345 A1 | 1/2017 | Kunz et al. | |
| 2017/0001402 A1 | 1/2017 | Kunz et al. | |

FOREIGN PATENT DOCUMENTS

| | | | | |
|---|---|---|---|---|
| EP | 0894604 A1 * | 2/1999 | ........... B29C 45/045 |
| EP | 1927452 | 6/2008 | |
| GB | 2185712 | 7/1987 | |
| GB | 2185712 A * | 7/1987 | ........... B29C 33/123 |
| JP | S60244513 | 12/1985 | |
| JP | H04193512 | 7/1992 | |
| JP | 2008168577 | 7/2008 | |
| WO | WO2005063143 | 7/2005 | |
| WO | WO2010106524 | 9/2010 | |
| WO | WO2012118489 | 9/2012 | |
| WO | WO2013141359 | 9/2013 | |

\* cited by examiner

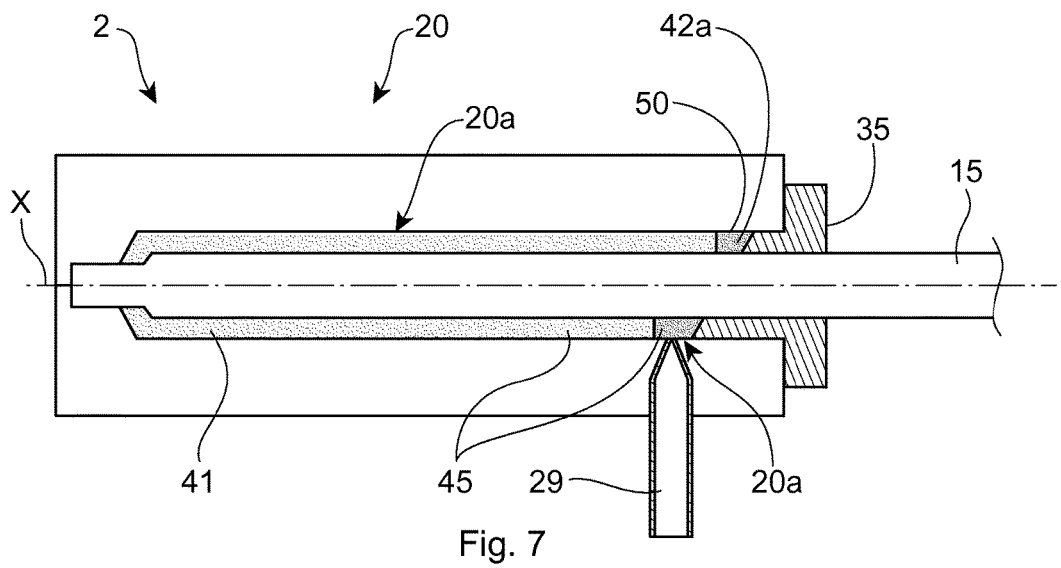
Fig. 7
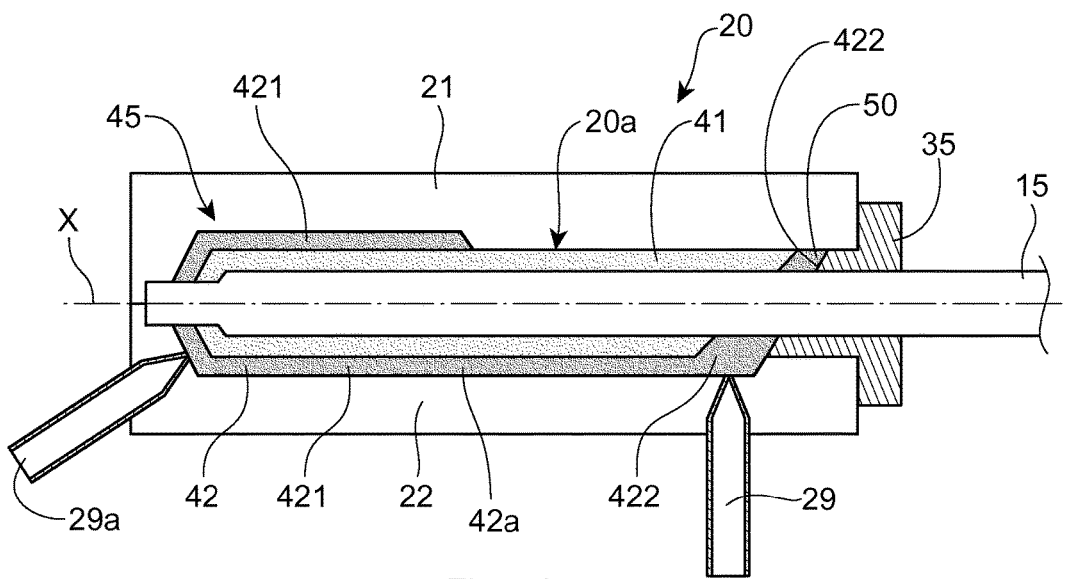
Fig. 7A
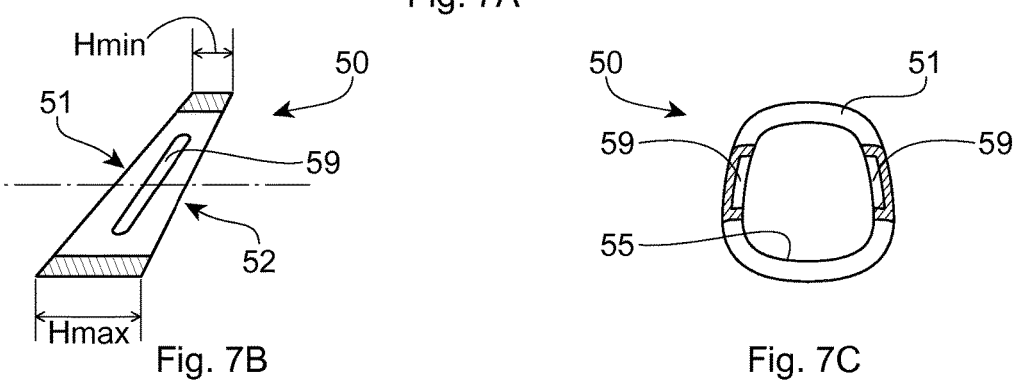
Fig. 7B
Fig. 7C

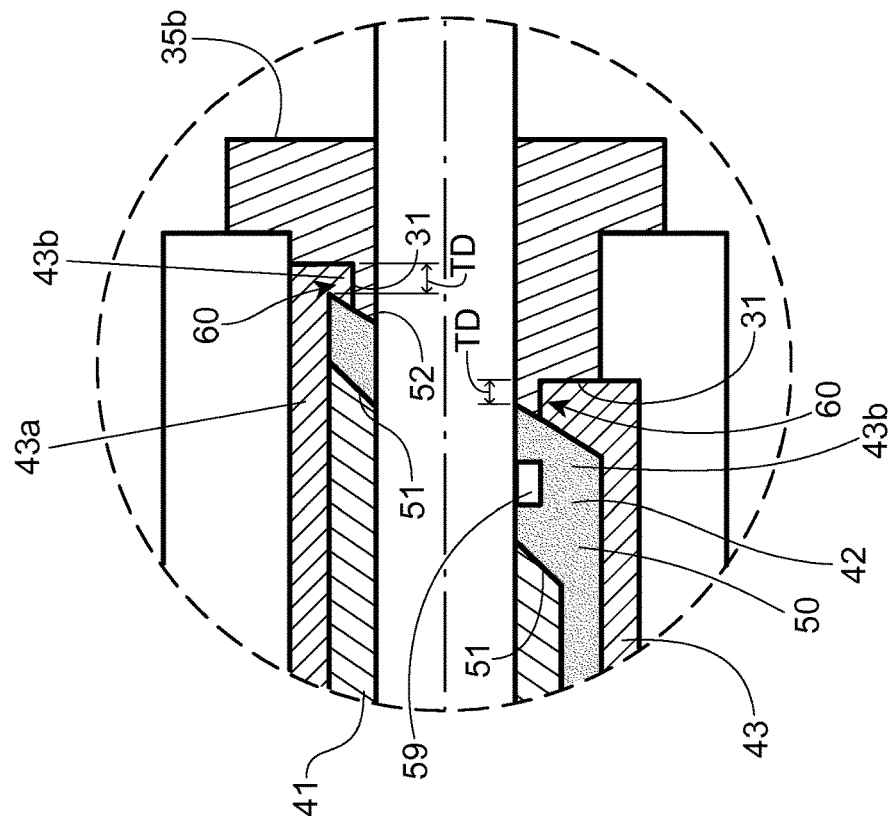
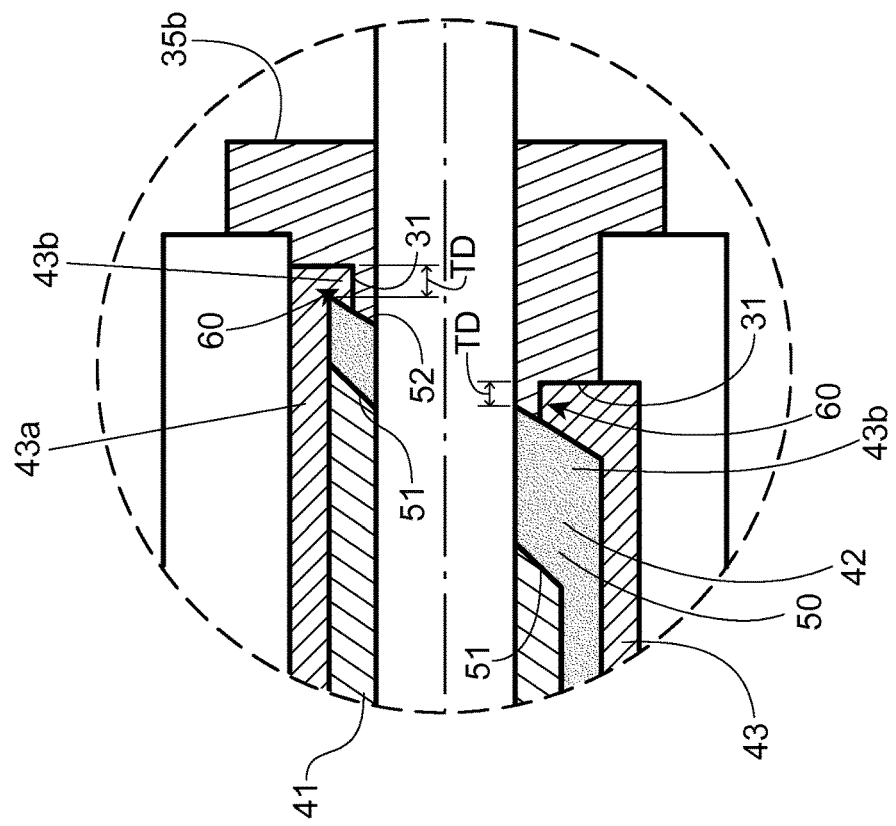

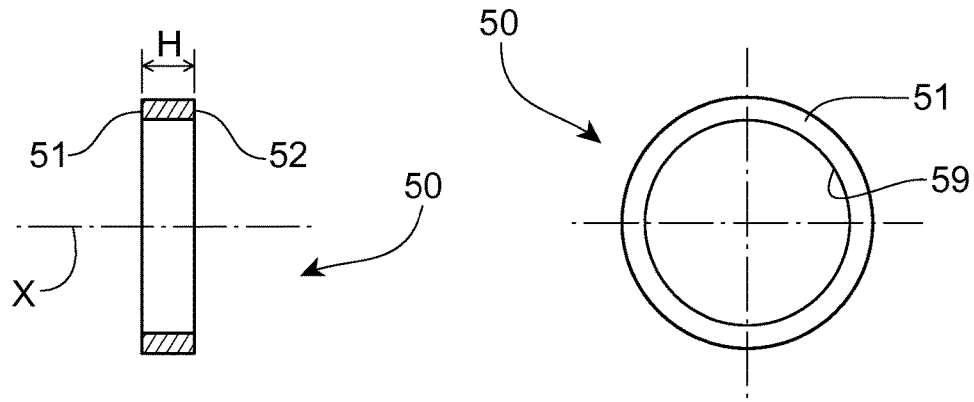
Fig. 9C
Fig. 9D
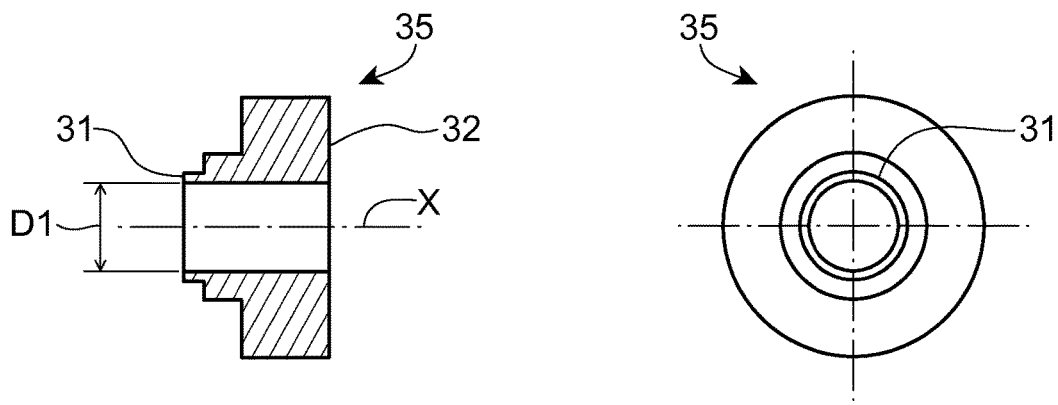
Fig. 10A
Fig. 10B
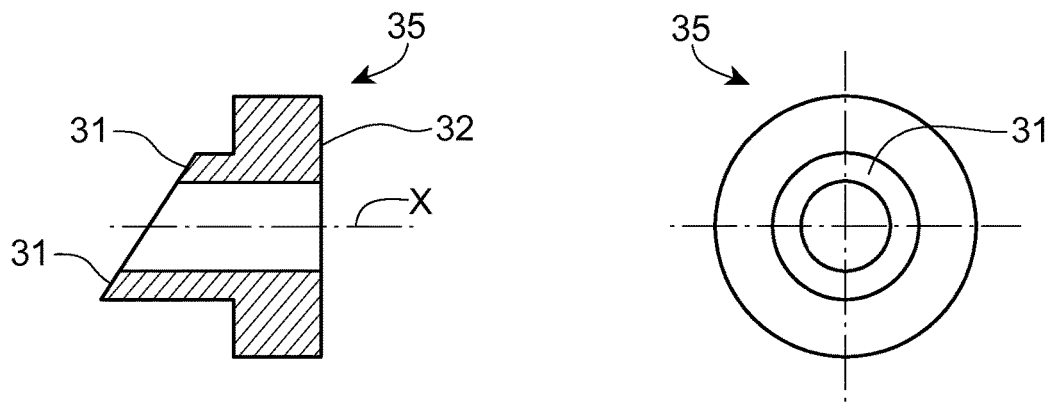
Fig. 11A
Fig. 11B

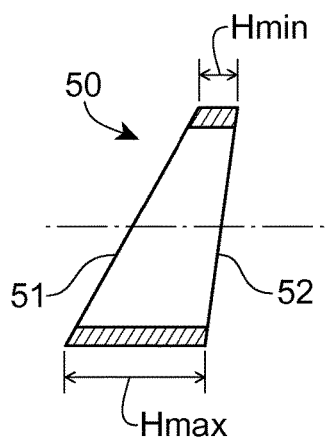
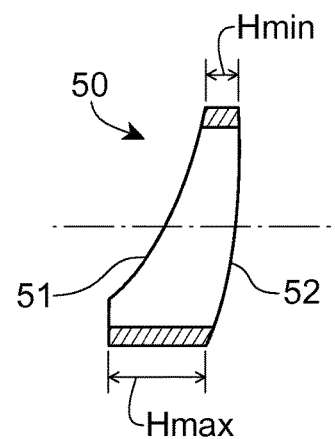
Fig. 14  Fig. 15
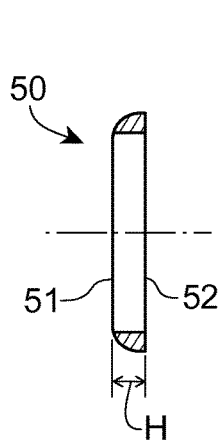
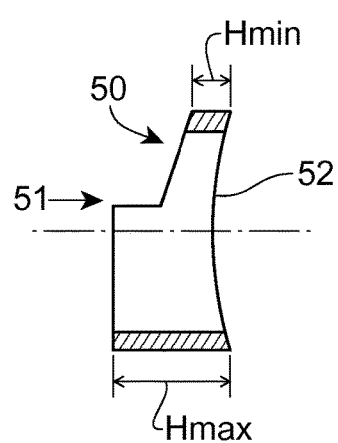
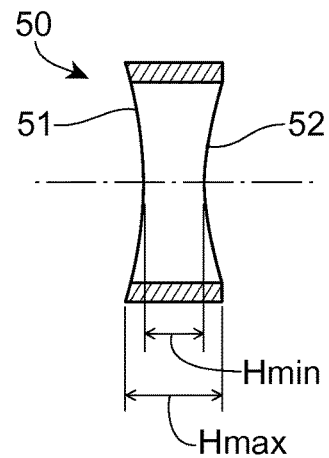
Fig. 16  Fig. 17  Fig. 18

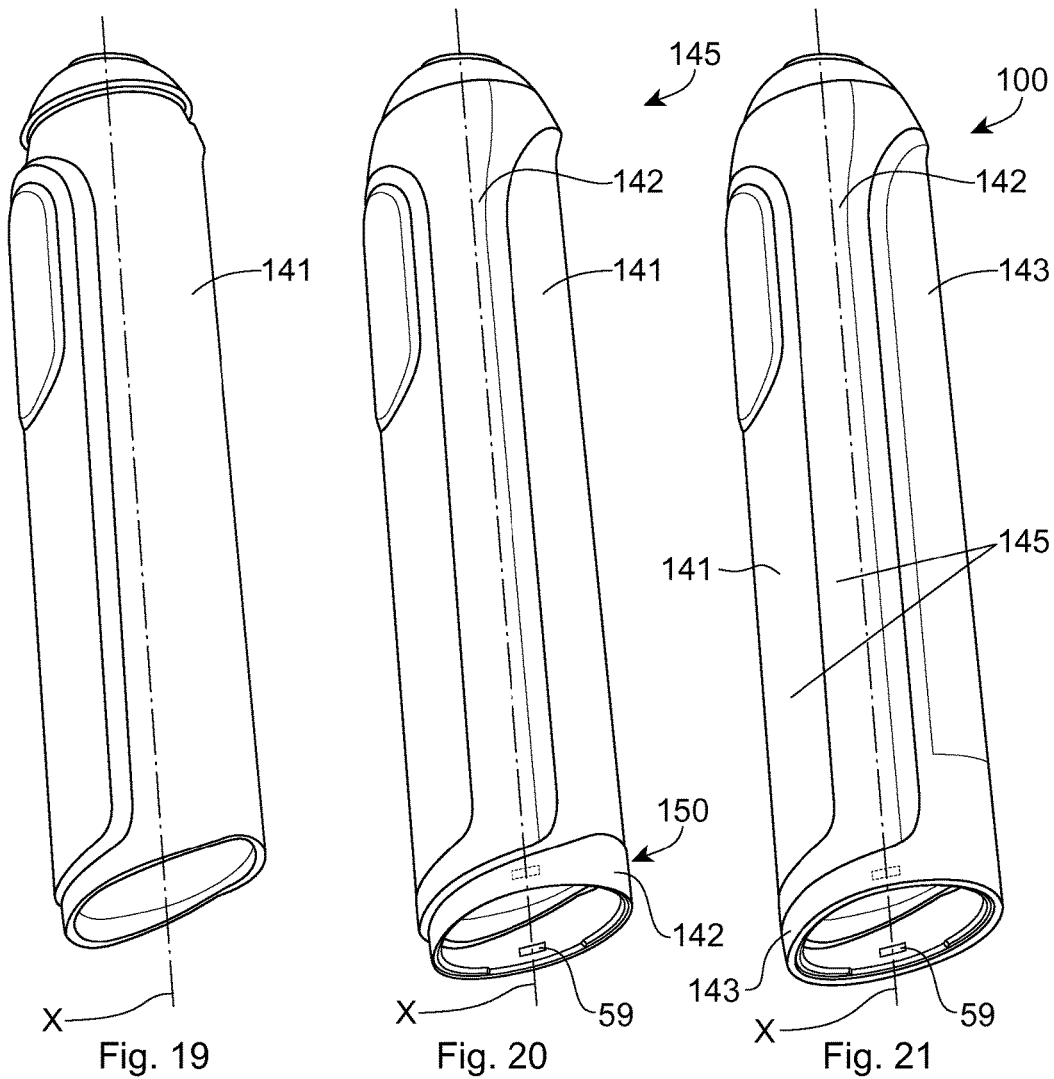

PLURALITY OF MASS-PRODUCED MULTI-COMPONENT PLASTIC HOUSINGS

FIELD OF THE INVENTION

The present disclosure is concerned with the mass manufacturing of multi-component plastic items made by injection molding, such as, e.g., those used as components for various power/electric tools, toothbrushes, and the like.

BACKGROUND OF THE INVENTION

Mass production of multi-component plastic items, such as, e.g., generally tubular toothbrush handles and other similar multi-component plastic elements, are typically made by a multi-step injection-molding process, wherein multiple molding steps are performed at multiple injection-molding stations. In the context of mass production of identical articles, those multi-component plastic elements, which will later become part or parts of the finished articles, are required to have a certain size and shape uniformity. This uniformity can be defined by the extent to which minute variations in corresponding shapes and sizes among the identical parts being successively injection-molded can be tolerated. The concern for uniformity is particularly important when the manufacturing process requires various molds to be involved—and becomes even more pronounced when multi-component parts that are required to be virtually identical are manufactured at multiple locations, which may have somewhat different manufacturing conditions as well as equipment and suppliers of the plastic material.

Virtually all plastic materials, after having being heated to be liquefied—and then cooled and solidified, typically shrink, thereby reducing their physical dimensions. This phenomenon is commonly referred to as "mold shrinkage." Since identical or similar plastic materials are expected to shrink proportionally to the same or similar degree, plastic parts having relatively greater dimensions shrink, in absolute numbers, to a greater extent relative to parts having relatively smaller dimensions. At the same time, while a shrinkage rate or percentage of shrinking for a certain material, such as, e.g., polypropylene (PP) or polypropylene (PE), can generally be known, it may be difficult to accurately predict the exact mold shrinkage beyond a "typical" shrinkage rate known for these materials. And the greater the dimension of the plastic material subjected of shrinkage, the more difficult it is to precisely predict the exact amount of shrinkage. This difficulty can be attributed to the following factors.

Shrinkage of a plastic part made by molding is believed to be likened to linear thermal contraction or expansion. When a mass of molten polymer is subjected to cooling, it contracts as the temperature drops. Holding pressure may be used to minimize shrinkage—but this can be effective only as long as the gate(s) remains open. If the polymer is homogeneous, all parts are expected to shrink proportionally even after the pressure is removed or the gates freeze off. This is what generally occurs with amorphous polymers, such as, e.g., polystyrene, polycarbonate, ABS, et cetera.

But PP and PE typically behave differently. Unlike amorphous polymers, PP and PE are not homogeneous materials—but are, instead, semi-crystalline materials, having a structure containing both amorphous components and crystalline components. Crystals normally shrink at rates higher than the rates at which the amorphous components shrink. Therefore, as these semi-crystalline materials, containing both amorphous and crystalline components, cool and solidify, they shrink at different rates. This imbalance typically results in a net increase in shrinkage and introduces sensitivity to molding parameters that may have additional effects on the shrinkage.

Another factor influencing shrinkage is believed to be linked to the viscoelastic characteristics of high-molecular-weight polymer melts in a mold. Long molecular-weight chains are stretched in the mold—and thus experience stress therein. During subsequent cooling, this stress is relieved, and the chains tend to relax. This relaxation influences the shrinkage, especially in differential flow directions. Both the average molecular weight and the molecular-weight distribution impact this aspect of mold shrinkage. Other variable factors that may influence shrinkage include thermal history of the molding, e.g., the melt temperature and cooling rate, as well as a thickness of the part being molded, gate dimensions, and other relevant factors.

In addition, plastic parts having a complex geometry, and especially those parts that comprise multiple layers of different plastic materials, tend to have differential shrinkage rates in different sections of the part. Although this phenomenon is largely pronounced during molding of parts having differential wall thickness, it may occur even in parts having relatively uniform wall thickness. The latter can be attributed, among other things, to non-uniform cooling and/or non-uniform filling patterns.

During a molding process of a multi-component part, such, e.g., as a toothbrush-handle housing or a power-tool housing, involving different molds, it may be necessary to place the part being made at different fixation geometries, i.e., mold cavities and/or mold cores. Molds having cores are naturally required for producing molding parts having a generally tubular geometry. A change of mold cavities is typically required to form a tubular part having multiple layers or components made of multiple plastic materials. A change of cores can also be required if one wishes to add one or more characteristics, geometries, or components to the inner surface of the tubular part being made, i.e., an area that is in contact with the core. Another reason for the change of the core in some instances may be dictated by a requirement that a following molding step is to be conducted on additional molding equipment incorporating another core.

If the part molded on a first molding tool needs to be transferred to a second molding tool for further molding/overmolding, this part's positioning in the second molding tool needs to be exact, allowing for very small tolerances. As used herein, the term "tolerance" refers to an allowable amount of variation of a specified measurable dimension, particularly a length dimension of a multi-component housing or any part thereof. As no item or any of its parts can be produced having dimensions precisely to the exact nominal value, tolerances are typically assigned to parts for manufacturing purposes, as boundaries for acceptable build.

Hence, there are acceptable degrees of deviation from the exact nominal value, suitable for a particular machine, process, or part. A manufactured part having dimensions that are out of tolerance will be unlikely a usable part for the intended purpose. Tolerances can be applied to any dimension. In the present context, lengthwise tolerances of a plastic part of parts, made by an injection-molding process, are of a particular interest. The exact positioning of the plastic part inside a mold is required to enable a reliably stable process and accurate touch-up lines between various molded components. The latter may greatly influence functional and aesthetic aspects of the finished product.

When the plastic part molded in one mold cavity is transferred to another mold cavity for further overmolding by another plastic material, one needs to take into account the fact that the length of the molten plastic part will likely change after it is cooled and solidified—as a result of the plastic material's shrinkage caused by cooling. If the shrinkage is significant, resulting in the solidified part being too short for a particular mold cavity, the mold parts intended to contact the part's surfaces may not reach those surfaces to provide a secure contact therebetween. The resulting undesirable empty spaces between the mold parts and the part's surfaces will likely cause "flashes" of the plastic material that is subsequently molded over the part that is too short.

Reversely, if the part being molded is too long for a subsequent mold cavity, the compression caused by the mold cavity's surfaces in contact with the part may crush the edges of the part being made. In addition, the mold may not be able to close completely and securely if the part disposed therein is too long for this mold. The latter may also lead to problems with the mold tool itself, including its premature ware and damage.

The mass production of the increasingly complex molded parts, such as, e.g., a multi-component handle part for a power toothbrush, requires successive changes of molds and/or mold cores. Such changes are required, e.g., when a previously molded part comprising a first plastic material needs to be at least partially overmolded with at least a second plastic material; and then the composite part, comprising the first and second plastic materials, needs to be further at least partially overmolded with at least a third plastic material, and possibly fourth plastic material, and so on.

These multiple successive molding steps require an exact positioning of the part being manufactured (i.e., molded/overmolded) step-by-step in every mold cavity and/or mold core that needs to be used in the process. To accomplish such an exact positioning, the manufacturer needs to make sure that the size and geometry of all elements, including the part being manufactured and the mold components used, match one another with a high-level precision, allowing for very small tolerance. These tolerances are often hard to achieve, particularly with respect to plastic parts affected by shrinkage, as is explained herein.

The exact positioning of the part being manufactured is particularly important in the context of a mass production that may take place at different locations. Such mass production requires multiple identical mold tools that are typically installed on different molding machines—all of which are intended for making identical parts. For example, for the injection molding of a power brush's handle, which is designed to house a motor, a battery, and electronics, as well as to have other functional attributes, the reliable uniformity and precision among the different molds, as well as the handle parts being made on those molds, are of high importance.

Therefore, current molding processes, which require a high degree of precision with respect to dimensions of a part or parts being made, tolerate only limited size and shape variations among the parts being manufactured. For example, a typical current injection-molding process used in the production of power-toothbrush handles is particularly sensitive to length variations of the plastic components. During cooling these components shrink, in absolute numbers, to a much greater extent in their lengthwise dimensions than they do in their dimensions extending perpendicularly to the lengthwise dimensions—due to the fact that their lengthwise dimensions are several times greater than their largest dimension perpendicular to their lengthwise dimensions.

For example, for some typical embodiments of the toothbrush handles, e.g., those having an overall length in the range of about 120-200 mm, and more specifically in the range of about 140-180 mm, the current molding process allows for lengthwise tolerance of not greater than ±0.2 mm in most of the successive molding operations. This may be difficult to maintain uniformly, particularly given the combination of all the factors and concerns described herein above.

SUMMARY

The present invention resolves this problem of the required tight tolerances during successive molding operations, and particularly lengthwise molding tolerances of plastic parts being molded and/or overmolded, by providing a process for manufacturing multi-component plastic structure that includes a novel functional element, a tolerance-elimination element. Moreover, the present invention allows manufacturers to significantly relax lengthwise tolerances for shrinkable plastic parts, thereby providing a more reliable and stable process of manufacturing multi-component plastic housings comprises those parts. The present invention also allows one to have reduced lengthwise tolerances of the finished item, thereby providing for a more consistent uniformity of lengthwise dimensions among mass-produced multi-component housings.

The tolerance-elimination element can be designed, structured, and configured to compensate for length deviations among plastic parts that are molded and overmolded in successive steps of the process and that are intended, in their solidified form, to be functionally and/or structurally identical to one another. These deviations are primarily caused, among other things, by differential shrinkage of the plastic materials used in the molding or overmolding steps. These deviations may also be caused by possible variation in the dimensions of the different mold tools, molding conditions, and other relevant factors. Thus, the tolerance-elimination element allows one to have much greater lengthwise discrepancies among the different plastic parts being molded, without negatively affecting the desired uniformity among a plurality of the final products and the consistency of their dimensions.

The tolerance-elimination element can be located at either end of the housing being made—and may include additional functional components therein, such as, e.g., engagement elements structured and configured to interconnect and hold together different parts of the item being made. Such engagement elements may include, e.g., mechanical locks, threads, projections, depressions, and the like. While the tolerance-elimination element can be incorporated at any end or both ends of the item, the present disclosure will focus on embodiments in which the tolerance-elimination element is located at a "bottom" end of the multi-component housing.

The tolerance-elimination element can be overmolded with a finishing plastic material, such as, e.g., a soft-plastic material, that would at least partially form an outer surface of the finished item. Such a finishing plastic material can be structured to cover the tolerance-elimination element either completely or partially, depending on a particular design of the item being made.

In one aspect, the present disclosure is directed to a process for making a multi-component hollow housing from a shrinkable plastic material. The multi-component housing can comprise at least three plastic materials. The finished housing has a top end, a bottom end, and a length therebetween that is parallel to a longitudinal axis of the housing and extends between the top and bottom ends thereof. The process comprises several steps.

A first plastic material can be injected into a first mold cavity having a first-cavity length. A mold core can at least partially be disposed in the first mold cavity. As the first plastic material solidifies, it shrinks lengthwise by a first absolute lengthwise shrinkage. The solidified first plastic material forms a first component, which comprises a generally tubular structure made of the first plastic material. The first component has a first end and a second end opposite to the first end and a first solidified length therebetween. The first solidified length of the shrunken first material is smaller than the first-cavity length.

Then the core, together with the first component disposed thereon, can be positioned in a second mold cavity. The second mold cavity has a second-cavity length that is greater than the first-cavity length by a distance greater than the first absolute lengthwise shrinkage of the first plastic material during solidification. A second plastic material can be injected into the second mold cavity and caused to solidify to form a second component made of the second plastic material and attached to the first component. The first and second components joined together form an intermediate part.

The second mold cavity can be structured to cause at least a portion of the second plastic material, injected into the second mold cavity, to form a tolerance-elimination element that is longitudinally adjacent to the first component at one of the first and second ends thereof. The tolerance-elimination element has a proximal end adjacent to the first component, a distal end opposite to the proximal end, and a length therebetween, which length can be constant—or alternatively can vary.

In embodiments wherein the tolerance-elimination element has an uneven length along its circumference, an average length can be calculated as an arithmetic mean of a maximal length and a minimal length of the tolerance-elimination element, the maximal and minimal lengths extending parallel to the longitudinal axis and between the proximal and distal ends of the tolerance-elimination element. In embodiments wherein the tolerance-elimination element has a constant length, this constant length constitutes an average length of the tolerance-elimination element, as well as its maximal length and its minimal length.

As the second plastic material forming the tolerance-elimination element solidifies, it too shrinks lengthwise. But the absolute lengthwise shrinkage of the second plastic material forming the tolerance-elimination element is at least ten times smaller than the first absolute lengthwise shrinkage of the first plastic material. The second mold cavity can be structured so that the maximal length of the tolerance-elimination element adjacent to the first component is at least ten times smaller than the first solidified length of the first component.

In a next step, the intermediate part, comprising the first and second component joined together, can be overmolded with a third plastic material in a third mold cavity. A solidified third plastic material forms a third component, made of the third plastic material and attached to at least one of the first component and the second component. In the resulting multi-component housing, comprising at least the first component, the second component, and the third component, the tolerance-elimination element is at least partially overmolded by the third plastic material, which forms at least a portion of an outer surface of the finished multi-component housing. Lastly, the multi-component housing can be removed from the core.

The second plastic material may be injected into the second mold cavity to form therein a first portion and a second portion, wherein the first portion of the second plastic material at least partially overmolds the first component, and the second portion of the second plastic material forms the tolerance-elimination element. In a further embodiment, both the first portion and the second portion of the second plastic material may be formed with a single injection shot. Alternatively, the first portion and the second portion of the second plastic material may be formed with two separate injection-molding shots, using two injection nozzles.

The first plastic material, the second plastic material, and the third plastic material may differ from one another in at least one characteristic selected from the group consisting of color, opacity, porosity, and hardness. Alternatively, at least two of the first, second, and third plastic materials may be identical to one another. In one embodiment, at least one of the first plastic material, the second plastic material, and the third plastic material is a hard-plastic material. In another embodiment, at least one of the first plastic material, the second plastic material, and the third plastic material is a soft-plastic material.

In one particular embodiment, the first plastic material is a first hard-plastic material, the second plastic material is a second hard-plastic material different from the first hard-plastic material, and the third plastic material is a soft-plastic material. Embodiments are contemplated in which the multi-component housing comprises more than the three plastic materials. In one such embodiment, the multi-component housing may comprise, e.g., a first hard-plastic material, a second hard-plastic material, a third soft-plastic material, and a fourth soft-plastic material, wherein the third and fourth soft-plastic materials overmold different areas or portions of the first and second hard-plastic materials. One of such areas or portions may comprise, e.g., an ON/OFF button or switches or other control elements, which are conventionally located on the housings, particularly those comprising power tools, such as power toothbrushes.

In one embodiment, an outer surface of the tolerance-elimination element is completely overmolded by the third plastic material so that the tolerance-elimination element does not form any part the finished item's outer surface. In another embodiment, the third material, which completely overmolds the tolerance-elimination element's outer surface, extends beyond a distal end of the tolerance-elimination element so that there is a distance between the third material's edge and the tolerance-elimination element's distal end. The formed distance can be from about 0.5 mm to about 3 mm.

In a further embodiment, the third plastic material may flow over a surface of the distal end of the tolerance-elimination element during the step of at least partially overmolding the combined intermediate part with a third plastic material. This would result in the third material at least partially overmolding the variable-ring distal end's surface. The surface of the distal end of the tolerance-elimination element can be perpendicular or inclined relative to the longitudinal axis of the housing.

In a further embodiment, the process may comprise positioning a sliding stripper on a mold core. Such a sliding stripper may be structured and configured to accomplish at least two functions: to form a part of a molding cavity during one of the injection-molding steps; and to slide along the core to remove or strip the finished item from the core. The sliding stripper can be structured, e.g., as a single-piece sleeve. Alternatively, the stripper can comprise more than one parts joined together on the mold core.

The stripper can be positioned at a distance from about 0.5 mm to about 3 mm from the distal end of the tolerance-elimination element, so that the third plastic material being injected and advancing in the mold cavity along the longitudinal axis is stopped by the stripper at a desired distance from the distal end of the tolerance-elimination element. Thus the stripper, by touching the third plastic material inside the mold cavity, can form an edge of the third plastic material when the third plastic material extends beyond the distal end of the tolerance-elimination element. The stripper's surface can be profiled to form a desired shape of the third plastic material's edge. In a final step of the process, the stripper can be caused to slide along the core to remove the multi-component housing from the core.

Depending on a particular embodiment of the housing being manufactured, the tolerance-elimination element can be shaped and sized to eliminate or greatly decrease size-related tolerances—particularly a lengthwise tolerance, related to the shrinkage of the plastic material during its cooling and solidification—that would otherwise be required for the purposes discussed herein above. In one embodiment, the tolerance-elimination element comprises a ring-type structure having a substantially even length along its circumference. The length of the tolerance-elimination element extends parallel to the longitudinal axis. Alternatively, the tolerance-elimination element can be beneficially shaped and sized to comprise a ring-type structure having uneven length along its circumference. Such an embodiment may be particularly useful in a multi-component housing having a relatively complex geometry.

In one embodiment, the tolerance-elimination element comprises a ring-type structure having a minimal length Hmin of from about 1 mm to about 20 mm and a maximal length Hmax of from about 10 mm to about 30 mm. In another embodiment, the tolerance-elimination element comprises a ring structure having an average length H of from about 3 mm to about 20 mm and from about 5 mm to about 10 mm.

In one exemplary embodiment, the tolerance-elimination element, structured and configured to have an average length H of about 5 mm, allows the multi-component housing having an overall length L of about 150 mm to have a very small lengthwise tolerance of less than 0.05 mm, and more specifically from about 0.01 mm to about 0.05 mm, or from about 0.007% to about 0.033%, depending on the plastic material and the process. A comparable multi-component housing made of the identical plastic materials—but lacking the tolerance-elimination element—would require a much greater lengthwise tolerance in order to accommodate the concerns related to the plastic material's shrinkage resulting from its cooling and solidification, as is described herein above.

Thus, the lengthwise tolerance needed for the comparable multi-component housing not having the tolerance-elimination element is from about 0.3 mm to about 1.5 mm in absolute numbers—or from about 0.2% to about 1.0% relative to the overall length of the comparable housing having an identical length L of about 150 mm. That is so because in the housing lacking the tolerance-elimination element the entire length of the housing, which shortens as a result of the shrinkage caused by solidification of the plastic material, needs to be taken into account for the purposes of tolerance, while in the housing of the invention, equipped with the tolerance-elimination element, only the tolerance-elimination element, which is several times shorter than the entire housing, is ultimately responsible for the shrinkage affecting tolerance.

In another aspect, the disclosure is directed to a process for making a multi-component housing for a toothbrush handle. Such housing can have a top end, a bottom end, a longitudinal axis, and a length extending parallel to the longitudinal axis and between the top and bottom ends. The housing can have several layers of plastic material, wherein some of the layers overmold one another, and wherein the plastic materials in at least some of the layers differ from one another.

The process for making a multi-component housing for a toothbrush handle comprises: injecting a first hard-plastic material into a first mold cavity having a core at least partially disposed therein, the first mold cavity having a first-cavity length; causing the first hard-plastic material to solidify, whereby the first hard-plastic material shrinks lengthwise by a first absolute lengthwise shrinkage and whereby a first component is formed, the first component comprising a generally tubular structure having a first end and a second end opposite to the first end and a first solidified length therebetween, wherein the first solidified length is smaller than the first-cavity length; positioning the core, together with the first component disposed thereon, in a second mold cavity having a second-cavity length that is greater than the first-cavity length by a distance greater than the first absolute lengthwise shrinkage of the first hard-plastic material; injecting a second hard-plastic material into the second mold cavity and causing the second hard-plastic material to solidify thereby forming a second component attached to the first component, the second component comprising a tolerance-elimination element that is longitudinally adjacent to the first component at one of the first and second ends thereof; wherein the tolerance-elimination element has a proximal end adjacent to the first component, a distal end opposite to the proximal end, and an average length that is arithmetic mean of a maximal length and a minimal length of the tolerance-elimination element, the maximal length and the minimal length extending parallel to the longitudinal axis and between the proximal and distal ends of the tolerance-elimination element, wherein the first solidified length of the first component is at least ten times greater than the maximal length of the tolerance-elimination element, and wherein an absolute lengthwise shrinkage of the second hard-plastic material forming the tolerance-elimination element is at least ten times smaller than the first absolute lengthwise shrinkage of the first hard-plastic material; at least partially overmolding the intermediate part with a soft-plastic material in a third mold cavity to form a third component attached to at least one of the first component and the second component, thereby forming the multi-component housing in which an outer surface of the tolerance-elimination element is at least partially overmolded by the soft-plastic material, and wherein the soft-plastic material forms at least a portion of an outer surface of the multi-component housing; and removing the multi-component housing from the core.

The second hard-plastic material can be injected to form a first portion and a second portion, wherein the first portion at least partially overmolds the first component comprising the first hard-plastic material, and the second portion forms the tolerance-elimination element adjacent to one of the first component's opposite ends. Both the first portion and the second portion of the second hard-plastic material can be formed with a single injection shot.

In one embodiment, the step of at least partially overmolding the combined intermediate part with a soft-plastic material results in the tolerance-elimination element being completely overmolded by the soft plastic material, so that the tolerance-elimination element does not form any part the finished toothbrush handle's outer surface—and cannot be seen under the surface of the soft-plastic material if the soft plastic material is sufficiently opaque.

The process may further comprise a step of positioning a sliding stripper that forms a part of the third mold cavity on a mold core. The sliding stripper can be positioned to abut the surface of the tolerance-elimination element. The sliding stripper can be positioned so that it touches the soft-plastic material being injected when the injected soft-plastic material is extending beyond the distal end of the tolerance-elimination element. By contacting the soft-plastic material, the surface of the sliding stripper facilitates the formation of an edge of the soft-plastic material. The sliding stripper's surface that contacts the soft-plastic material can be configured to profiled the edge of the soft-plastic material in a desired manner. In one embodiment, a distance of from about 0.5 mm to about 3 mm can be formed between the edge of the soft-plastic material in contact with at least a portion of the stripper and at least a portion of the distal end of the tolerance-elimination element. In a further embodiment, a surface of the distal end of the tolerance-elimination element can be at least partially overmolded by the soft-plastic material. The surface of the distal end of the tolerance-elimination element is oriented orthogonally relative to the longitudinal axis of the housing. As used herein, the terms "orthogonal," "orthogonally," and any variations thereof refer to dimensions or orientations that are not substantially parallel to the longitudinal axis—and that include those perpendicular or inclined (at greater or lower than 90 degrees angles) relative to the longitudinal axis of the housing. At the end of the process, the sliding stripper can move the housing along the mold core thereby stripping the finished housing from the core. Depending on the process, one or more sliding strippers can be utilized.

During cooling of the second hard-plastic material, the tolerance-elimination element shrinks, in absolute length, to a much smaller extent than the first and/or second materials would have shrunk in a comparable housing constructed without the tolerance-elimination element. This much smaller shrinkage of the tolerance-elimination element is due to the fact that the tolerance-elimination element is much shorter than the housing as a whole. Even though relative or proportional lengthwise shrinkage (as a percentage of the length) of the tolerance-elimination element on the one hand and the housing without the tolerance-elimination element on the other hand can be similar or identical, the absolute lengthwise shrinkage of the tolerance-elimination element is much lower than that of the entire housing.

In one embodiment, the resulting multi-component housing for the toothbrush handle has a lengthwise tolerance of from 0.01 mm to 0.05 mm. In another embodiment, the resulting multi-component housing for the toothbrush handle has a lengthwise tolerance of from of from about 0.006% to about 0.03% relative to the length L of the multi-component housing.

In one embodiment, after the second hard-plastic material has solidified, the tolerance-elimination element has the longitudinal minimal length Hmin of from about 1 mm to about 20 mm. In another embodiment, after the second hard-plastic material has solidified, the tolerance-elimination element has the longitudinal minimal length Hmin of from about 2 mm to about 15 mm. In a further embodiment, after the second hard-plastic material has solidified, the tolerance-elimination element has the longitudinal minimal length Hmin of from about 3 mm to about 10 mm. The longitudinal maximal length Hmax of the solidified tolerance-elimination element can be from about 10 mm to about 30 mm.

The first hard-plastic material and the second hard-plastic material may differ from one another in at least one characteristic selected from the group consisting of color, opacity, porosity, and hardness. But an embodiment is contemplated, in which the first hard-plastic material and the second hard-plastic material are identical. In one specific embodiment, at least one of the first hard-plastic material and the second hard-plastic material is transparent or translucent, and the soft material is opaque.

In a further aspect, the disclosure is directed to a multi-component housing comprising at least a first component, a second component, and a third component. The first component comprises a first plastic material and has a first end and a second end opposite to the first end. The second component comprises a second plastic material. The third component comprises a third plastic material. The at least first, second, and third components are joined together to form a substantially tubular structure having a longitudinal axis, a top end and a bottom end opposite to the top end, a length L parallel to the longitudinal axis and extending between the top end and the bottom end, and a maximal orthogonal dimension Dmax extending perpendicular to the longitudinal axis. The length L of the housing is at least three times greater than the maximal orthogonal dimension Dmax extending perpendicular to the longitudinal axis.

The housing includes at least one tolerance-elimination element made of the second plastic material and attached to one of the first and second ends of the first component along the longitudinal axis. The tolerance-elimination element has a proximal end and a distal end opposite thereto. The proximal end is adjacent to at least one of the first and second ends of the first component. The tolerance-elimination element has an average length H, parallel to the longitudinal axis, extending between the proximal end and the distal end. The average length H is at least ten times less than the length L of the housing. The third component at least partially forms an outer surface of the housing, so that the tolerance-elimination element is at least partially overmolded by the third plastic material.

As used herein, the term "maximal orthogonal dimension" of the housing (or any of its elements) refers to the housing's (or any of its elements') largest dimension measured substantially perpendicular to the longitudinal axis of the housing. For example, in a housing structured as a regular cylindrical tube the maximal orthogonal dimension is the housing's outer diameter.

In another aspect, the disclosure is directed to a multi-component housing for a toothbrush handle. The multi-component housing for a toothbrush handle has a top end, a bottom end opposite to the top end, and a longitudinal axis therebetween. The housing also has a length L of from about 120 mm to about 200 mm extending between the top and bottom ends and a maximal orthogonal dimension Dmax extending perpendicular to the longitudinal axis. The length L of the housing is at least three times greater than the maximal orthogonal dimension Dmax extending perpendicular to the longitudinal axis.

The housing comprises at least a first component made of a first hard-plastic material and having a first end and a second end opposite thereto, a second component made of a second hard-plastic material, and a third component made of a soft-plastic material. The first component, the second component, and the third component are integrally joined together to form a generally tubular structure.

The housing includes at least one tolerance-elimination element made of the second plastic material and attached to one of the first and second ends of the first component along the longitudinal axis. The tolerance-elimination element has a proximal end adjacent to the first component and a distal end opposite to the proximal end. The tolerance-elimination element may be at least partially overmolded by the soft-plastic material. The tolerance-elimination element has an average length H of from about 3 mm to about 20 mm extending parallel to the longitudinal axis between the proximal end and the distal end of the tolerance-elimination element. The tolerance-elimination element causes the housing to have a lengthwise tolerance of from about 0.006% to about 0.03% relative to the length L of the housing.

In its further aspect, the disclosure is directed to a plurality of mass-produced identical multi-component housings, as is described herein above, wherein the tolerance-elimination elements of the plurality of multi-component housings cause the individual housings to have lengthwise maximal dimension variations of the length L to be not greater than 0.1 mm among the individual multi-component housings. In some embodiments, the average length H of the tolerance-elimination elements of the plurality of the mass-produced housings varies among at least some of the tolerance-elimination elements by a lengthwise dimension that is at least ten times greater than the lengthwise maximal dimension variations of the length L among the individual multi-component housings.

In another aspect, the disclosure is directed to a plurality of mass-produced identical multi-component housings for toothbrush handles, as is described herein above, wherein the tolerance-elimination element in each of the multi-component housings is structured to cause the individual housing to have a lengthwise tolerance of from about 0.006% to about 0.03% relative to the length L of the housing. For multi-component housings typically having a nominal overall length of from about 120 mm to about 200 mm and constructed to form handles of power toothbrushes or other power tools, the multi-component housings are expected to have a lengthwise tolerance of not greater than 0.05 mm in absolute numbers—and lengthwise maximal dimension variations of the overall lengths among the individual multi-component housings are expected to be not greater than 0.1 mm. In relative terms, the multi-component housings can have a lengthwise tolerance of from about 0.006% to about 0.03% relative to the nominal overall length of the multi-component housing, and lengthwise maximal variations in length of from about 0.012% to about 0.06% among the individual housings.

In its final aspect, the disclosure is directed to a power toothbrush comprising a handle and a removable attachment having cleaning elements thereon, wherein the handle comprises a multi-component housing described herein and structured and configured to receive therein an electric motor, a battery, and various drive components to power the removable attachment. In one embodiment, the tolerance-elimination element has an interior surface that includes engagement elements formed therein and structured to interconnect different parts of the power toothbrush. Beneficially, the tolerance-elimination element can be completely overmolded by the soft-plastic material so that the tolerance-elimination element does not form any part of the outer surface of the toothbrush handle and is not visible under the surface of the soft-plastic material if the soft-plastic material is opaque.

BRIEF DESCRIPTION OF THE DRAWINGS

While the specification concludes with claims which particularly point out and distinctly claim the subject matter that is regarded as the invention, the various embodiments will be better understood from the following description taken in conjunction with the accompanying drawings, in which:

FIG. 7 is a schematic cross-sectional view of a second molding station shown in FIG. 5, having the first component disposed therein, and showing a subsequent step of the process, comprising overmolding the first component with a second plastic material to form a combined intermediate part comprising the first and second component joined together, wherein the second plastic material forms a tolerance-elimination element adjacent to one of the ends of the first component.

FIG. 7A is a schematic cross-sectional view of another embodiment of a second molding station shown in FIG. 5, having the first component disposed therein, and showing a subsequent step of the process comprising overmolding the first component with a second plastic material to form a combined intermediate part comprising the first and second component joined together, wherein the second plastic material comprises a first portion that at least partially overmolds the first component and a second portion that forms the tolerance-elimination element adjacent to one of the ends of the first component.

FIG. 7B is an enlarged cross-sectional view of the embodiment of the tolerance-elimination element shown in FIG. 7A.

FIG. 7C is a front view of the embodiment of the tolerance-elimination element shown in FIG. 7B, wherein the shown front view includes a partial cross-section showing grooves formed on an interior surfaces of the tolerance-elimination element.

FIG. 8B is an enlarged portion of the cross-section shown in FIG. 8 and showing a fragmental view 8B, wherein the third plastic material completely overmolds the outer surface of the tolerance-elimination element and extends beyond a distant end thereof.

FIG. 8C is an enlarged portion of the cross-section similar to that shown in FIG. 8, and showing an embodiment in which the tolerance-elimination element has an undercut.

FIG. 9C is an enlarged cross-sectional view of an embodiment of the tolerance-elimination element shown in FIG. 9A.

FIG. 9D is a front view of the tolerance-elimination element shown in FIG. 9C.

FIG. 10A is a schematic cross-sectional view of an exemplary embodiment of a stripper that can be part of the mold tool of the third mold station.

FIG. 10B is a front view of the stripper shown in FIG. 10A.

FIG. 11A is a schematic cross-sectional view of another exemplary embodiment of a stripper that can be part of the mold tool of the third mold station.

FIG. 11B is a front view of the stripper shown in FIG. 11A.

FIG. 14 is a schematic cross-sectional view of a first exemplary embodiment of the tolerance-elimination device.

FIG. 15 is a schematic cross-sectional view of a second exemplary embodiment of the tolerance-elimination device.

FIG. 16 is a schematic cross-sectional view of a third exemplary embodiment of the tolerance-elimination device.

FIG. 17 is a schematic cross-sectional view of a fourth exemplary embodiment of the tolerance-elimination device.

FIG. 18 is a schematic cross-sectional view of a fifth exemplary embodiment of the tolerance-elimination device.

FIG. 19 is a schematic perspective view of an embodiment of a partially made handle of a toothbrush, comprising a first component made of a first plastic material.

FIG. 20 is a schematic perspective view of the embodiment shown in FIG. 14, comprising the first component made of the first plastic material, a second component made of a second plastic material, and including a tolerance-elimination element made of the second plastic material.

FIG. 21 is a schematic perspective view of the embodiment shown in FIGS. 14 and 15, and comprising the first component made of the first plastic material, the second component made of the second plastic material, and a third component made of a third plastic material, wherein the third plastic material completely covers an outside surface of the tolerance-elimination element.

DETAILED DESCRIPTION

Figure 1:
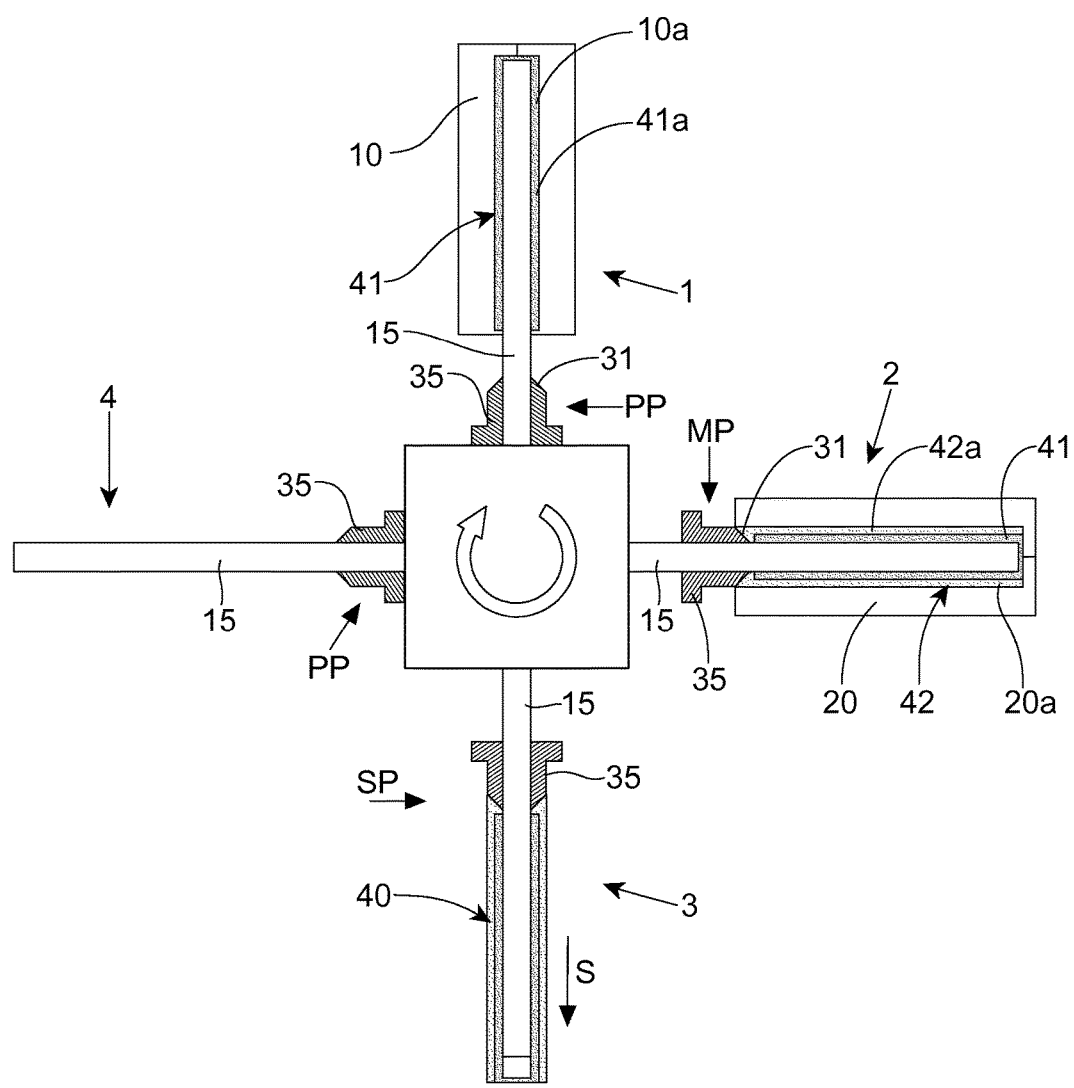
FIG. 1 is a schematic plan view of an embodiment of a molding device and a process for making a multi-component housing that does not utilize a tolerance-elimination element, the molding device including two molding stations and one stripping station.

The following description does not attempt to list every possible embodiment of the invention because that would be impractical if not impossible. This disclosure, therefore, is to be construed as exemplary, that is, any feature, characteristic, structure, component, or step described herein can be combined with or substituted for, in whole or in part, any other feature, characteristic, structure, component, or step described herein. It should also be understood that the relative scale of some elements shown in the drawings may not be exact, i.e., a thickness of plastic components shown in the several exemplary embodiments is purposefully exaggerated for the purposes of illustration.

An exemplary molding device, and its components, for manufacturing multi-component housing 100, or a plurality 200 of multi-component housings 100, are variously shown in FIGS. 1-9. FIGS. 1-3B schematically show an embodiment of an exemplary process, wherein the multi-component housing (shown in FIG. 4) is manufactured without utilizing a tolerance-elimination element. FIGS. 5-9B schematically show embodiments of an exemplary process of the disclosure, wherein various multi-component housings (examples of which are shown in FIGS. 7A, 8, 8A, 9A, and 19-21) can be manufactured with a tolerance-elimination element.

The multi-component housing 100 comprises an essentially hollow structure, manufactured by step-by-step injection molding. The injection-molding process uses different mold cavities and typically a single mold core that can be transferred, together with the plastic structure being made, from one mold cavity to another. The core is structured and configured to be at least partially located inside the mold cavities during the various steps of the process. Hence, one end of the core can be covered by the plastic material being injected into a mold cavity—and eventually by the hollow part being made, while the other end of the core is not covered by eth plastic material. The end of the core that is located inside the mold cavities and that is covered with the plastic material is termed herein a first end of the core; and the opposite end is a second end of the core.

Figure 5:
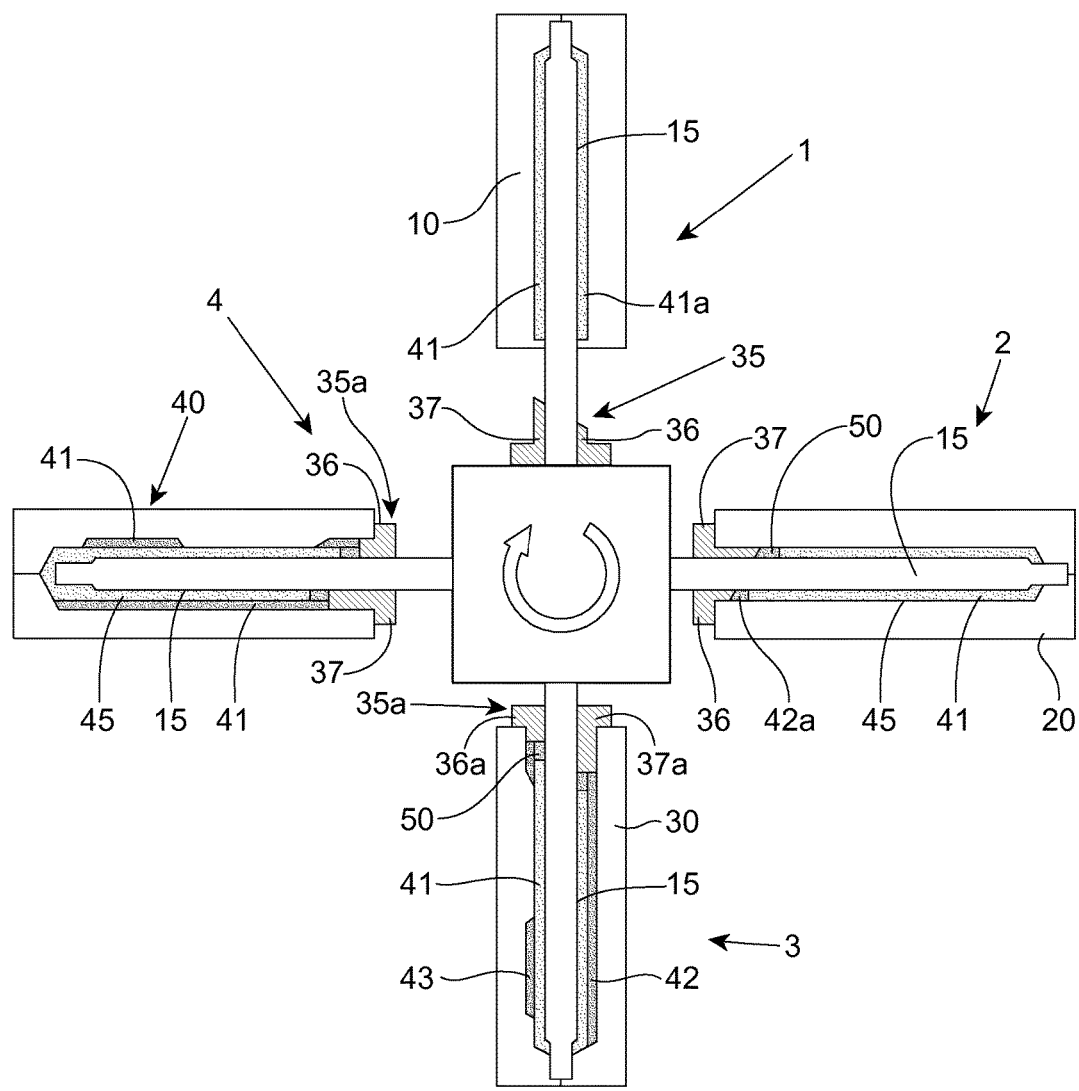
FIG. 5 is a schematic plan view of another embodiment of a molding device and a process of the present disclosure for making a multi-component housing that comprises a tolerance-elimination element, wherein the molding device includes three molding stations and one stripping station.

The molding device, a plan view of which is schematically shown in FIGS. 1 and 5, may comprise two or more molding stations. In an exemplary embodiment of the process shown in FIG. 1, the molding device comprises two molding stations 1, 2 and one stripping station 3. In an exemplary embodiment of the process of the invention shown in FIG. 4, the molding device comprises three molding stations 1, 2, 3 and one stripping station 4. Each molding station has a mold cavity configured to form a certain portion of the hosing being made.

These successive portions may comprise layers, partial layers, and localized plastic parts made of various plastic materials formed in the successive molding steps. The layers and parts of the housing being made that have already been injected and formed on the core can be transferred from one molding station to another, i.e., by moving the core from one station to the next one. To this end, the injection-molding stations may be arranged adjacent to one another, e.g., in a linear manufacturing line (not shown), wherein the core can be conventionally transferred, from station to station, from the beginning of the manufacturing line to the end thereof.

Alternatively, the molding stations may be arranged along a circular path, as is schematically shown in FIGS. 1 and 5. The stations may be arranged, e.g., along a circle or a rectangle, and the core can be transferred from one station to another by rotation. The degree of a single-step rotation can be chosen depending on the number of molding stations arranged around a circular or rectangular path. Thus, e.g., a single-step rotation of 90° can be naturally used in the molding device comprising four stations arranged equiangularly from one another (FIGS. 1 and 5).

After the molding process is complete, the hollow housing, still disposed on the core, can be removed therefrom. A sliding stripper, located at the second end of the core, can be structured and configured to accomplish this task of removing, or stripping the finished housing from the core. To this end, the stripper can be moved along the core in the direction of the first end of the core.

The stripper can be also structured and configured to form a part of at least one of the mold cavities during the injection-molding process occurring in that cavity. Thus, the stripper can slide along the core—and can be positioned in more than one place on the core. In one embodiment, the stripper can travel along the core to be located, e.g., in three different positions on the core.

The stripper may be structured as a single-part complete or partial sleeve or ring. Alternatively, the stripper can be structured to comprise more than one part. The stripper may be made of any suitable heat-resistant material capable of withstanding the temperatures of hot-melted plastic materials. One non-limiting example of such a heat-resistant material is stainless steel.

It should be understood that while the disclosure refers mostly to a single stripper, more than one stripper could be arranged on the core, depending on the process and equipment. For example, two different, similar, or identical strippers can be located at opposite sides of the core. Since the stripper can comprise a part of a mold cavity, different strippers can be used in different molding operations or in different mold cavities to form different elements of the housing being manufactured. If two or more strippers are used in the molding device disclosed herein, all strippers can be movable and all can be structured to accomplish the functions disclosed herein.

The stripper can be arranged on the core in at least three different positions: passive position, molding position, and demolding or stripping position. In a passive position, the stripper is arranged near the second end of the core, outside the mold cavity. In a molding position, the stripper forms a part of the mold. In other words, when the mold is closed, a "molding" surface of a first end of the stripper facing the mold comprises a part of a surface of the mold cavity that contacts the plastic material injected into the mold cavity. To put it another way, the stripper in the molding position is arranged on the core to close or seal the mold cavity at one end. Because the first end of the stripper forms a part of the mold cavity's surface, the shape of the stripper's first end can be profiled to form a desired surface, which would be contacted by the plastic material to form a mirror surface of the surface of the stripper's first end.

The stripper's molding surface may include, e.g., various inclined surfaces, recesses, projections, and the like. Thus, complex parts, such as, e.g., undercuts and inclined depressions, can be formed relatively easily during the injection-molding process. If more than one stripper is used, the strippers may have differently shaped first ends, which would allow one to form differently shaped parts of the housing being made. Also, multiple strippers may be located at their molding positions at different locations on the core in order, so that different parts of the housing being made could be easily formed. Of course, if all of the multiple strippers have identical first ends that are arranged at identical molding positions, a plurality of identically shaped parts can be formed for the housing being made.

FIGS. 10A-13B show several exemplary designs of a stripper 35. While all the exemplary strippers shown are configured for a cylindrical mold core, it should be appreciated that any suitable shapes of the stripper's inner orifice designed to fit a corresponding core can be had. An embodiment of the stripper 35 shown in FIGS. 10A and 10B has an inner diameter D1 and a first end 31 that is planar and substantially perpendicular to the longitudinal axis X of the core (not shown). An embodiment of the stripper 35 shown in FIGS. 11A and 11B has first end 31 that is planar and inclined relative to the longitudinal axis X of the core (not shown). An embodiment of the stripper 35 shown in FIGS. 12A and 12B has a first end 31 that is concave and inclined. An embodiment of the stripper 35 shown in FIGS. 13A and 13B (shown apart and disengaged from a core 15 for illustration) comprises two parts, a first part 36 and a second part 37. The first part 36 has a flat first end 31a that is substantially perpendicular to the longitudinal axis X of the core 15, while the second part 37 has a first end 31b that is convexly shaped and is inclined relative to the longitudinal axis X of the core 15.

In a demolding or stripping position, the stripper is positioned on the core to remove the finished item. The demolding position is the position that is nearest to the first end of the core. In other words, the distance from the first end of the core to the first end of the stripper in the demolding position is smaller than the size of the hollow part. In particular, the distance is smaller enough to allow the stripper to strip the housing from the core. If more than one stripper is used in the process, the demolding position of multiple strippers relative to the core may be identical or different. If, e.g., the injected hollow part is asymmetrical or irregular, the demolding positions of the strippers may be adapted to the dimension of the housing.

As is known in the art, each of the mold cavities of the molding device may be formed by multiple parts. The mold cavity may, e.g., be formed by a first mold half and a second mold half. As used herein, a "mold half" means any part that forms a limiting surface or a part thereof of the mold cavity. In that sense, the mold "half" may greater or smaller than the mold's real physical half. In addition, the volume of the mold cavity is also limited by the core, which is located at least partially in the mold cavity. The plastic material can be injected into the mold cavity by one or several injection nozzles, as is known in the art.

FIG. 1 shows an exemplary embodiment of a molding device comprising a first molding station 1, a second molding station 2, and a demolding or stripping station 3. The first molding station 1 is shown with a first plastic material 41a already injected onto a core 15 in a first mold cavity 10a of a first mold 10, to form a first plastic component 41. A movable stripper 35 is arranged on the core 15 in a passive position PP outside the first mold 10.

The second molding station 2 is shown, likewise, after a second plastic material 42a has been injected into a mold cavity 20a of a second mold 20, to form a second plastic component 42 that at least partially covers or "overmolds" the first plastic component 41. The stripper 35 has now moved on the core 15 to be in its molding position MP, whereby a "molding" surface of the first end 31 of the stripper 35 forms a part of the interior surface of the mold cavity 20a.

At the demolding or stripping station 3, the stripper 35 removes, or strips a finished housing 40 from the core 15. Here, the stripper 35 is arranged on the core 15 in its demolding position DP, whereby the stripper 35, being in contact with the housing 40, travels towards the first end of the core 15, thereby removing the housing 40 from the core 15. An arrow "Y" indicates the stripper's movement along the core 15 as the stripper removes the housing 40 therefrom. The finished housing 40 comprises a substantially hollow structure composed by a first component 41 at least partially overmolded by a second component 42.

At a fourth position 4, the movable stripper 35 rests in its passive position PP on the core 15. From here, the core 15 can be transferred to the first station by a 90-degree rotational step, and the injection-molding process can be repeated.

Figure 2A:
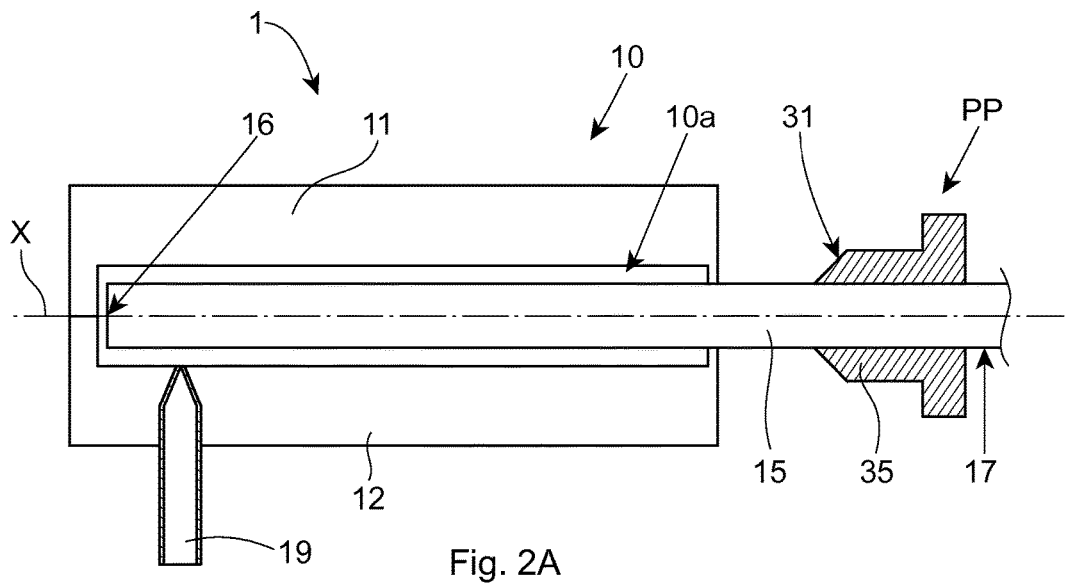
FIG. 2A is a schematic cross-sectional view of a first molding station shown in FIG. 1, before a first plastic material has been injected into a first mold cavity.

FIG. 2A shows an enlarged cross-sectional view of the first molding station 1 before the first plastic material 41a has been injected thereto. The first mold 10 comprises a first mold half 11 and a second mold half 12, which are arranged to form the first mold cavity 10a. A first injection nozzle 19 is shown as passing through the second mold half 12 into the first mold cavity 13. The core 15 is arranged with its first end 16 disposed inside the first mold cavity 10a. The sliding stripper 35, in contact with a surface 17 of the core 15, is arranged in its passive position PP outside the first mold cavity 10a.

Figure 2B:
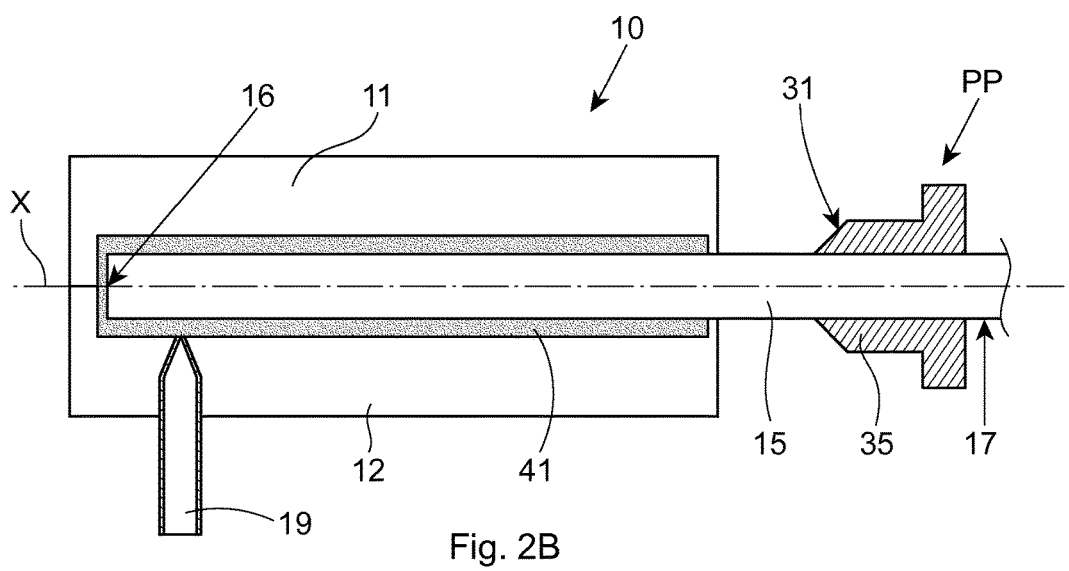
FIG. 2B is a schematic cross-sectional view of a first molding station shown in FIG. 2A, after the first plastic material has been injected into the first mold cavity.

FIG. 2B shows an enlarged cross-sectional view of the first molding station 1 after a first plastic material 41a, in its melted form, has been injected, through the nozzle 19, into the first mold cavity 10a, to form a first plastic component 41 therein. The stripper 35 rests in its passive position PP outside the mold 10.

Figure 3A:
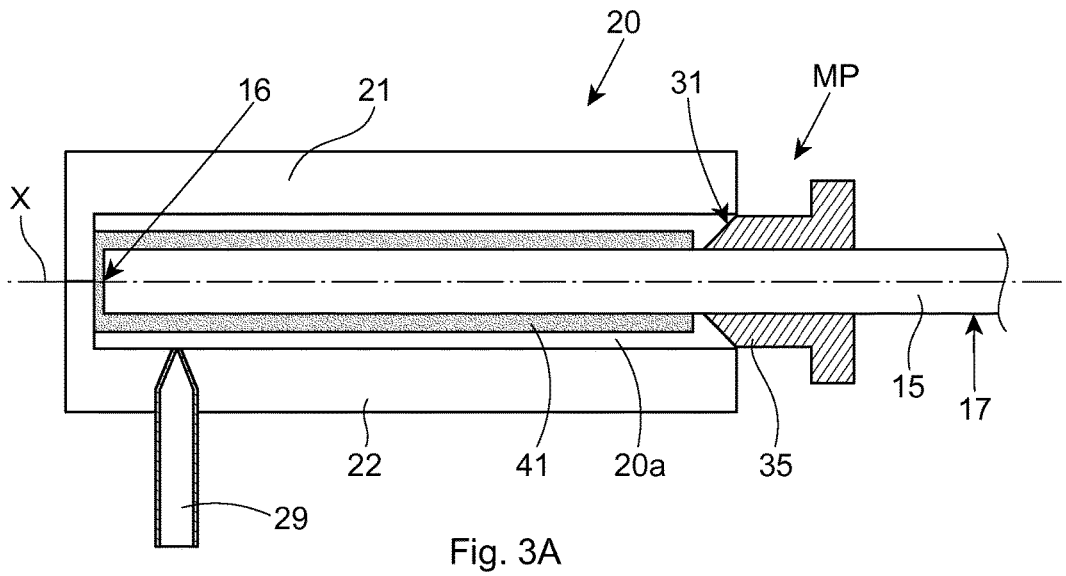
FIG. 3A is a schematic cross-sectional view of a second molding station shown in FIG. 1 and having therein the first component disposed on the mold core, before a second plastic material has been injected into a second mold cavity to at least partially overmold the first component.

FIG. 3A shows an enlarged cross-sectional view of the second molding station 2 before the second plastic material has been injected thereto. The second mold 20 comprises a first mold half 21 and a second mold half 22, which are arranged to form the second mold cavity 20a. A second injection nozzle 29 is shown as passing through the second mold half 22 into the second mold cavity 20a. The core 15, carrying the first plastic portion 41, made of the first plastic material 41a, is arranged with its first end 16 inside the second mold cavity 20a. The sliding stripper 35 is moved into its molding position MP, wherein the molding surface of the stripper's first end 31 forms a part of the mold 20. In the exemplary embodiment of the stripper 35 shown in FIGS. 3A and 3B, the surface of the first end 31 of the stripper 35 is inclined, but one skilled in the art would appreciate that the first end 31 of the stripper 35 can be shaped in any desired manner.

Figure 3B:
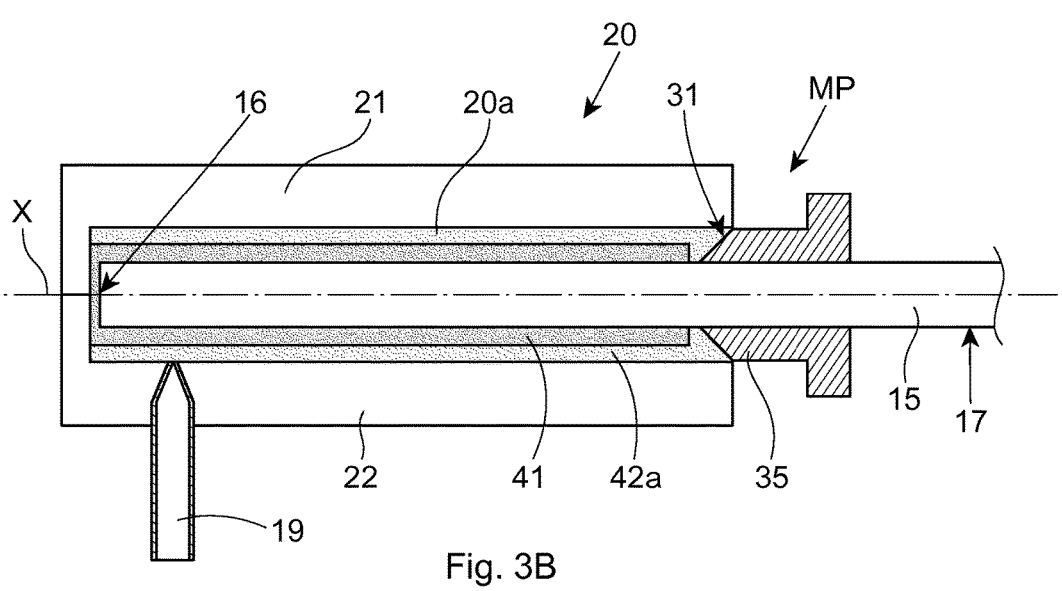
FIG. 3B is a schematic cross-sectional view of a second molding station shown in FIG. 3A after the second plastic material has been injected into the second mold cavity.
Figure 4:
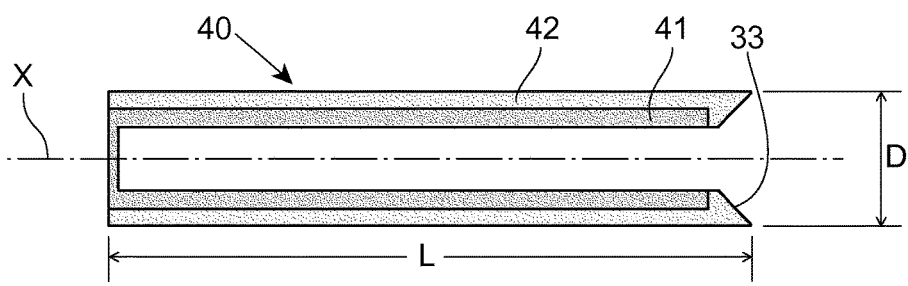
FIG. 4 is a schematic cross-sectional view of a multi-component housing made by a process illustrated in FIGS. 1-3B, wherein the housing has been made without the tolerance-elimination element, and wherein the housing's length is at least three times greater than the housing's maximal orthogonal dimension extending perpendicular to the longitudinal axis of the housing.

FIG. 3B shows an enlarged cross-sectional view of the second molding station 2 after the second plastic material 42a has been injected thereto through the second injection nozzle 29, to form the second plastic component 42 joined to the first plastic component 41. Depending on the design of the multi-component housing being made, the second plastic material 42a can be injected to fully or partially overmold the first component's outer surface, which is not in contact with the core 15. In FIG. 3B, the stripper 35, arranged in its molding position MP adjacent to the second mold 20, forms a part of the second mold cavity 20a. The inclined surface of the stripper's first end 31 in contact with the second plastic material 42a forms a corresponding undercut 33 in the second portion 42 of a resulting multi-component housing 40 (FIG. 4), comprising the first component 41 and the second component 42.

FIG. 5 shows an embodiment of a molding device similar to that shown in FIGS. 1-3B—but illustrating a novel process of the invention, wherein the tolerance-elimination element is utilized in the construction of the multi-component housing 100 being made. The movable stripper 35, in this exemplary embodiment, comprises at least two parts, or "halves": a first stripper part 36 and a second stripper part 37, which can be structured to move either in unison or independently from one another, depending on the process. This type the stripper 30 is illustrated in more detail in FIGS. 13A and 13B.

Figure 6:
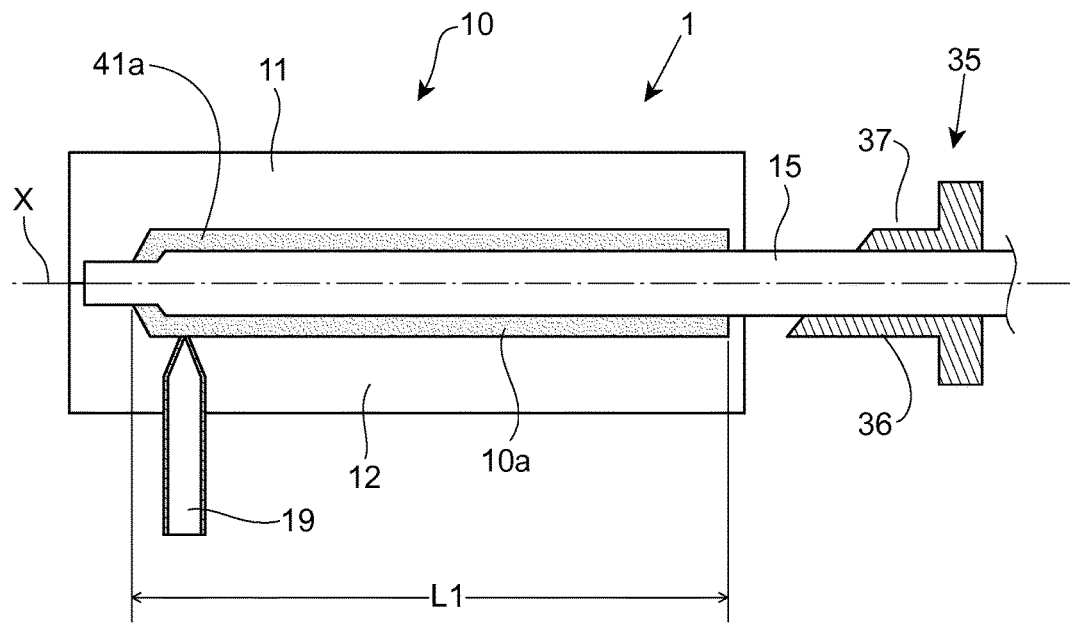
FIG. 6 is a schematic cross-sectional view of a first molding station shown in FIG. 5, and of a step of a process comprising injection-molding of a first plastic material into a first mold cavity to form a first component.
Figure 6A:
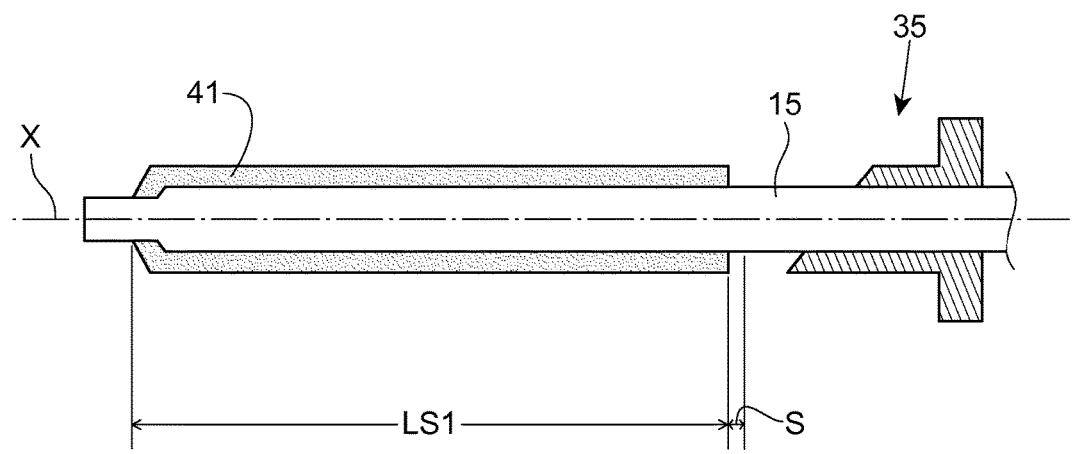
FIG. 6A is a schematic cross-sectional view of the first molding component comprising a solidified first plastic material.

A first molding station 1 is shown in FIGS. 5 and 6 after the first plastic material 41a has been injected onto the core 15 in the first mold cavity 10a of the first mold 10. The first mold cavity 10a has a first-cavity length L1 (FIG. 6). During cooling and solidification, the first plastic material 41a shrinks, as is explained herein above. The resulting first component 41, comprising the solidified first plastic material 41a, has a first solidified length LS1 that is smaller than the first-cavity length L1 by an amount of the longitudinal shrinkage S (FIG. 6A). The first component 41 may have any suitable wall thickness, which may be constant throughout the first component 41—or alternatively may vary. In one exemplary embodiment, particularly suitable for a multi-component housing designed for a toothbrush handle, the first component 41 may have a thickness of from about 0.5 mm to about 2.5 mm, and more specifically from about 0.9 mm to about 1.9 mm.

For example, a plastic material comprising polypropylene and having a length of about 150 mm and an average thickness of about 0.7-2.4 mm in its liquid state is expected to lose, during solidification, from about 0.3 mm to about 1.5 mm in absolute numbers (depending on the process conditions, the average being about 0.6 mm)—or from about 0.2% to about 1.0% of its original length. Naturally, the first component 41 in this instance will have the average solidified length LS1=150.0 mm−0.6 mm=149.4 mm. At the upper limit of the shrinkage range, the first component 41 will have the average solidified length LS1 of about 148.5 mm (150.0 mm−1.5 mm=148.5 mm). To eliminate or significantly minimize the lengthwise tolerance caused by such a substantial shrinkage, the process of the disclosure utilizes a tolerance-elimination element that is designed to at least partially absorb, or even eliminate altogether, length deviations affecting solidified plastic components caused by the shrinkage of the plastic material comprising those components.

A second molding station 2 is shown in FIGS. 5 and 7 after the second plastic material 42a has been injected into the second mold cavity 20a of the second mold 20, to form a combined intermediate part 45, comprising the first component 41 and the second component 42 joined together. The second component 42 may have any suitable wall thickness, which may be either constant or vary throughout the second component 42. In one exemplary embodiment, particularly suitable for a multi-component housing designed for a toothbrush handle, the second component 42 may have a thickness of from about 0.5 mm to about 2.5 mm, and more specifically from about 1.0 mm to about 1.6 mm.

The intermediate part 45, likewise, may have any suitable, constant or varying, wall thickness. One skilled in the art will understand that in embodiments in which the intermediate part 45 is formed by one or more plastic materials overmolding one or more components, i.e., embodiments comprising two or more layers of plastic materials/components in at least some portions of the housing, the resulting thickness of the housing in those portions will comprise a sum of thicknesses of the relevant layers of the plastic materials. In one exemplary embodiment, particularly suitable for a multi-component housing designed for a toothbrush handle, the first component 42 may have a thickness of from about 0.8 mm to about 2.5 mm, and more specifically from about 1.0 mm to about 1.2 mm.

The second component 42 includes the tolerance-elimination element 50 that is integrally attached to one of the ends of the first component 41. The molten second plastic material 42a being injected into the second mold cavity 20a flows into, and at least partially occupies, the space created by the shrinkage of the first material 41a. The second plastic material 42a contacts the first component 41 and integrally attaches thereto. Thus, the second material 42a that occupies the "shrinkage" space absorbs the shrinkage. When the second plastic material 42a solidifies to form the tolerance-elimination element 50, it also experiences some degree of shrinkage. However, because the tolerance-elimination element 50 is many times shorter than the first component 41, the lengthwise shrinkage affecting the tolerance-elimination element 50 is many times less that the lengthwise shrinkage of the first plastic material 41a.

In the context of mass production of a plurality of multi-component identical housings, the average length H, the maximal length Hmax, and the minimal length Hmin of individual tolerance-elimination elements will vary, depending on the individual amounts of the first material's shrinkage absorbed by the individual tolerance-elimination elements. Thus, the individual tolerance-elimination elements in the plurality of finished mass-produced multi-component housings may differ from one another lengthwise to a much greater extent than their respective lengthwise shrinkage would otherwise cause.

In the finished housings, however, the length variations will be primarily defined by the lengthwise shrinkage differential among the individual tolerance-elimination elements. This lengthwise shrinkage differential is at least ten times less than that among the individual first components, assuming comparable shrinkage rate between the first and second plastic materials and at least the 10X difference in length between the first component and the tolerance-elimination element. Thus, in the plurality of mass-produces multi-component housings the average length H, the maximal length Hmax, and the minimal length Hmin will vary among at least some of the tolerance-elimination elements by a lengthwise dimension that is at least ten times greater than the lengthwise maximal dimension variations of the length L among the individual multi-component housings in the plurality.

Assuming that the rates of shrinkage of first material 41a (comprising the first component 41) and the second material 42a (comprising the tolerance-elimination element 50) are generally comparable, the absolute shrinkage differential between the first component 41 and the tolerance-elimination element 50 can be expected to be approximately proportional to the length differential between the two. If, e.g., the first component 41 were about ten times longer than the tolerance-elimination element 50, the lengthwise shrinkage of the former would be expected to be about ten times greater than that of the latter.

In addition, at least in some embodiments, a plastic material having a rate of shrinkage proportionally smaller than that of the first plastic material 41a can be selected as the second plastic material 42a, which forms the tolerance-elimination element 50. In such instances, the absolute lengthwise shrinkage of the tolerance-elimination element 50 would be even smaller than that of a material having a shrinkage rate proportionally comparable with that of the first plastic material 41a. Such a second plastic material 42a, having a proportionally lower rate of shrinkage, might not be suitable or desirable for forming substantially larger or functionally different portion or portions of the housing because of one or more undesirable properties that may be inherent in such a low-shrinkage material. Such a material, however, may be acceptable for the purposes of forming a relatively short part of the housing comprising the tolerance-elimination element 50, particularly if the latter will not be visible in the finished housing, and will not be otherwise affecting its appearance and quality.

FIG. 7A schematically illustrates another embodiment of a second molding station 20 and the step of the process of the invention. Here, the intermediate part 45, comprising the first and second components 41, 42 joined together, includes a first portion 421 and a second portion 422 of the second plastic material 42a (or the second plastic component 42). The first portion 421 at least partially overmolds the first component 41 and the second portion 422 forms the tolerance-elimination element 50 adjacent to one of the ends of the first component 41. It should be understood that the terms "first portion 421" and "second portion 422" are used in the present context conventionally, for the purposes of illustration; in some embodiments, such as, e.g., the one shown in FIG. 7A, there may be no well-defined, exact boundary or border separating the first portion 421 from the second portion 422, and the second component 42 as a whole can be a single element in which the first and second portions 421, 422 are integrally connected.

In the exemplary embodiment of FIG. 7A, each of the first portion 421 and the second portion 422 of the second plastic material 42a is shown as being injected primarily via a separate injection nozzle: a nozzle 29a injecting primarily the first portion 421 and a nozzle 29b injecting primarily the second portion 422. But it should be appreciated that in other possible embodiments, the two portions 421, 422 of the second plastic material 42a can be injected via a single injection nozzle and/or with a single injection shot. All of these embodiments are within the scope of this invention.

One embodiment of an exemplary tolerance-elimination element 50 is schematically shown in FIGS. 7B and 7C. The tolerance-elimination element 50 shown comprises a ring-type structure having a proximal end 51 and a distal end 52 opposite to the proximal end 51. In the mold 20, the proximal end 51 is adjacent to one of the ends of the first component 41. The shape of interior walls 55 of the tolerance-elimination element 50 reflects the shape of a portion of the mold core 15 on which the tolerance-elimination element 50 has been formed; and the shape of exterior walls 56 of the tolerance-elimination element 50 reflects the shape of a portion of the second mold cavity 20a in which the tolerance-elimination element 50 has been formed.

Therefore, if the tolerance-elimination element 50 needs to be structured to have additional functional attributes, such as, e.g., a fastening means and the like, which can be used for attaching the housing to another element of an item of which the housing is designed to be a part of, then the relevant portions of the core 15 and/or the mold cavity 20a need to be profiled accordingly. The exemplary embodiment of the tolerance-elimination element 50 shown in FIGS. 7B and 7C has two mutually opposite grooves or undercuts 59, formed in the interior walls 55.

While the tolerance-elimination element 50 shown in FIGS. 7A and 7B has an essentially symmetrical (relative to an imaginary vertical axis) front face (FIG. 7C), comprising the proximal end 51, one skilled in the art would appreciate that the shape of the tolerance-elimination element is largely dictated by the shape of the multi-component housing being made and other considerations described herein. Thus, any suitable shape of the tolerance-elimination element is contemplated by this invention.

Such shapes may include circular, rectangular, triangular, multi-angular, elliptical, oval, et cetera geometrical shapes of any desired and suitable proportions and combination thereof, as well as symmetrical, asymmetrical, and irregular shapes. In an exemplary embodiment shown in FIGS. 9C and 9B, the tolerance-elimination element 50 comprises an essentially symmetrical ring structure having a constant length H throughout its circumference. In such an instance, it can be said that the maximal length Hmax, minimal length Hmin and the average length H are equal.

At the same time, the tolerance-elimination element 50 shown in FIGS. 7B and 7C has an uneven length, ranging from a minimal length Hmin to a maximal length Hmax. In some embodiments, an average length H of the tolerance-elimination element having more than one length can be calculated as an arithmetic mean of the Hmax and Hmin, i.e., H=½(Hmin+Hmax). While a gradual change of length is shown in the embodiment of FIGS. 7B and 7C, it is contemplated that various other embodiments of the tolerance-elimination element 50 may have discrete and/or otherwise irregular or convoluted changes of the length throughout the circumference of the tolerance-elimination element 50. As used herein, the term "circumference" refers to the enclosing boundary of a curved geometric figure, which may comprises, in whole or in part, any shape, not limited to a circle.

As is explained herein, the shape of the tolerance-elimination element is principally dictated by the shape of the multi-component housing being made. FIG. 17 illustrates one exemplary embodiment of the tolerance-elimination element 50 having such non-gradual change of its length, from Hmin to Hmax. Likewise, while the embodiment of FIGS. 7B, 7C illustrate the tolerance-elimination element 50 in which the minimal length Hmin is directly opposite to the maximal length Hmax, i.e., the minimal length Hmin and the maximal length Hmax are disposed at 180 degrees relative to one another, embodiments are contemplated in which the minimal and maximal lengths Hmin, Hmax are not directly opposite to one another—but instead are located on the circumference of the tolerance-elimination element at an angle that is less or greater than 180 degrees relative to one another, as is shown in an exemplary embodiment of FIG. 18.

Figure 8:
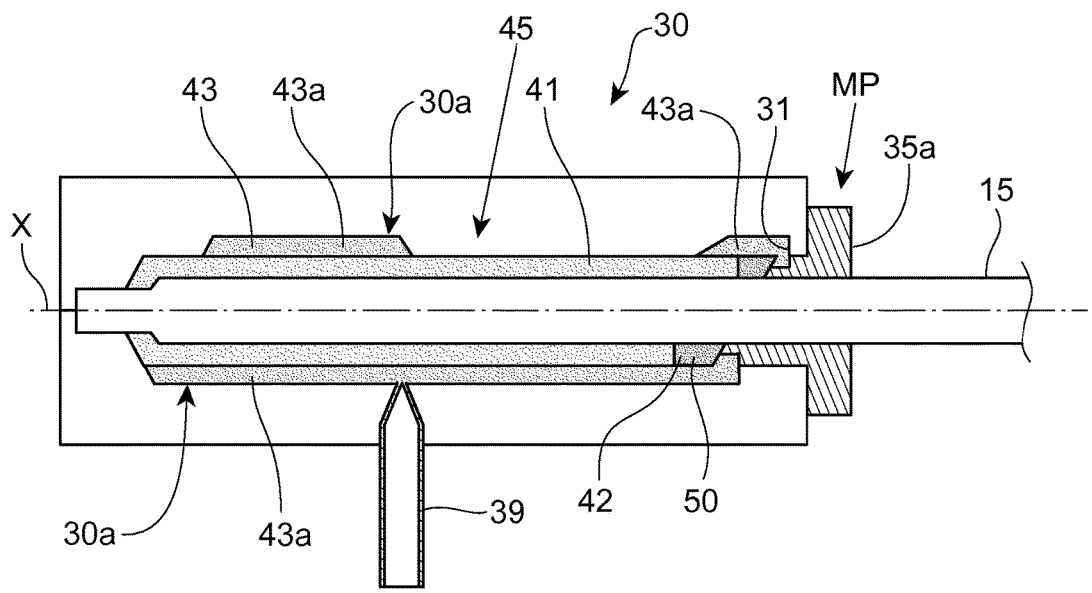
FIG. 8 is a schematic cross-sectional view of a third molding station shown in FIG. 5, having the intermediate part of FIG. 7 disposed therein, and showing a subsequent step of the process, comprising overmolding the intermediate part with a third plastic material to form a multi-component housing, wherein the third plastic material at least partially overmolds the tolerance-elimination element.

In FIG. 8, a third molding station 30 is shown after the third plastic material 43a has been injected thereinto to at least partially overmold the intermediate part 45, including the tolerance-elimination element 50, formed by the second plastic material 42a. A movable stripper 35a is arranged on the core 15 in its molding position, to form a part of the third mold 30. That is, a surface of the first end of the stripper 35a forms a portion of the third mold cavity's surface intended to contact the third plastic material 43a being injected into the third mold cavity 30a. While a stripper 35a, different from the stripper 35, is shown in this exemplary embodiment, one skilled in the art would appreciate that the single stripper 35 can be used throughout the process. Utilization of a single stripper may be particularly beneficial for those embodiments of the process in which the stripper is connected to, or form a part of, an index plate.

Figure 8A:
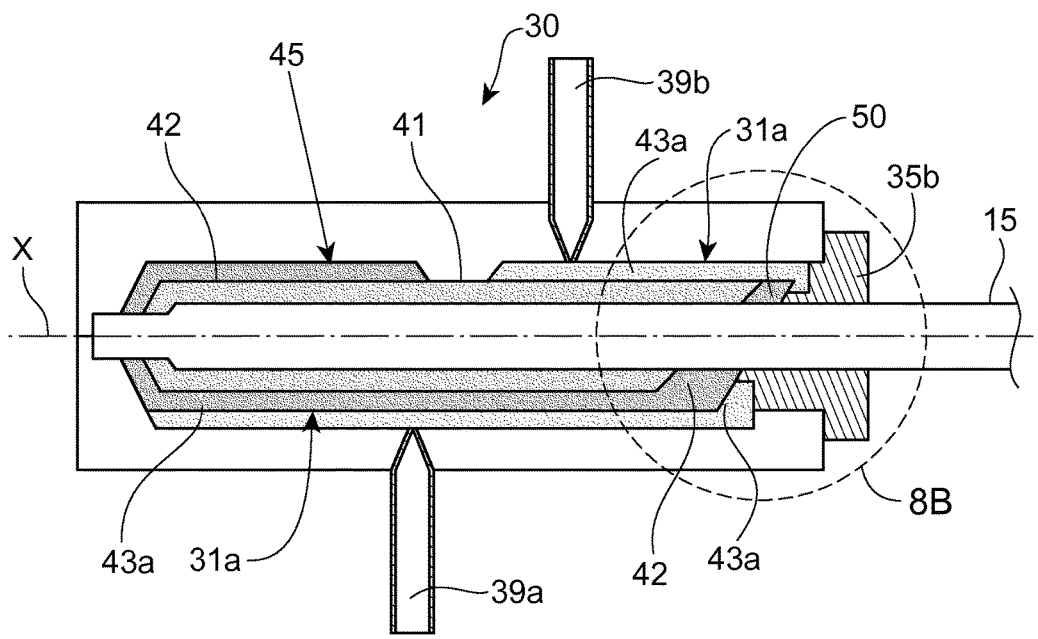
FIG. 8A is a schematic cross-sectional view of another exemplary embodiment the third molding station shown in FIG. 5, having the intermediate part of FIG. 7A disposed therein, and showing a subsequent step of the process, comprising overmolding the intermediate part with a third plastic material to form a multi-component housing, wherein the third plastic material at least partially overmolds the tolerance-elimination element, and wherein the multi-component housing has a length that is at least three times greater than the housing's maximal orthogonal dimension.

FIG. 8A shows another exemplary embodiment the third molding station 30 having the intermediate part 45 disposed therein and showing the step of overmolding the intermediate part 45 with a third plastic material 43a. The movable stripper 35a is arranged on the core 15 in its molding position, to form a part of the third mold 30. In this embodiment the third material 43a covers the intermediate part 45 in a pattern different from the overmolding pattern shown in FIG. 8. Also, in this exemplary embodiment, the third material 43a is injected into the third mold 30 through two separate injection nozzles, 39a and 39b, disposed at opposite sides of the third mold.

FIG. 8B shows an enlarged view of a fragment of the cross-section shown in FIG. 8A, to illustrate a manner in which the third plastic material 30 can be caused to completely overmold the outer surface of the tolerance-elimination element 50—and even extend beyond a distant end 52 thereof, into a touch-up area 60. The surface of the first end 31 of the stripper 35b stops the advance of the molten third plastic material 43a. A similar fragment, in the context of another embodiment, is shown in FIG. 9B.

FIG. 8C shows an enlarged fragmental view similar to the one shown in FIG. 8, but showing a further embodiment of the tolerance-elimination element 50. In the embodiment of FIG. 8C, the tolerance-elimination element is constructed to have an undercut 59. For the purposes of illustration, the undercut 59 is shown only on one side of the tolerance-elimination element 50, but embodiments are contemplated in which two or more undercuts can be had on the tolerance-elimination element 50. Also, an embodiment is contemplated in which an undercut extends to the full circumference of the tolerance-elimination element, although such a configuration would likely require a forced demolding. In one specific embodiment, particularly suited for a toothbrush housing, the tolerance-elimination element 50 can have two undercuts 59 (FIGS. 20, 21)—for the fixation of the bottom closure. Such undercuts can be made, e.g., by utilizing a slider in the core (not shown).

Relative dimensions of all cooperating parts, such as the shape and depth of the third mold cavity, the size and shape of the tolerance-elimination element 30, the shape and position of the first end 31 of the stripper 35b, and the like elements, can be beneficially designed to allow the third plastic material 43a to slightly extend beyond the distal end of the tolerance-elimination element, comprising an edge of the intermediate part 45, to form a touch-up portion or portions 43b disposed between a portion of the first end 31 of the stripper 35a and a portion of the distal end 52 of the tolerance-elimination element 50. The tolerance-elimination element 50 is beneficial as the intermediate part has low longitudinal tolerances and thus compression of the intermediate part or flashes during overmolding are avoided. Embodiments in which the third plastic material 43a does not extend beyond the distal end 32 of the tolerance-elimination element 50 are also contemplated. In such embodiments, the third plastic material 43a can flush with the distal end 32 of the tolerance-elimination element 50.

If the first end 31 does not touch the tolerance-elimination element 50 (FIG. 9B), a touch-up distance TD can be formed between an edge of the third plastic material 43a in contact with the stripper's first end 31 and the distal end 52 of the tolerance-elimination element 50. In one embodiment, the touch-up distance can be from about 0.5 mm to about 3 mm. In another embodiment, the touch-up distance TD can from about 1 mm to about 2 mm. In a further embodiment, the touch-up distance can be as small as between about 0.1 mm and about 0.5 mm.

Figure 9:
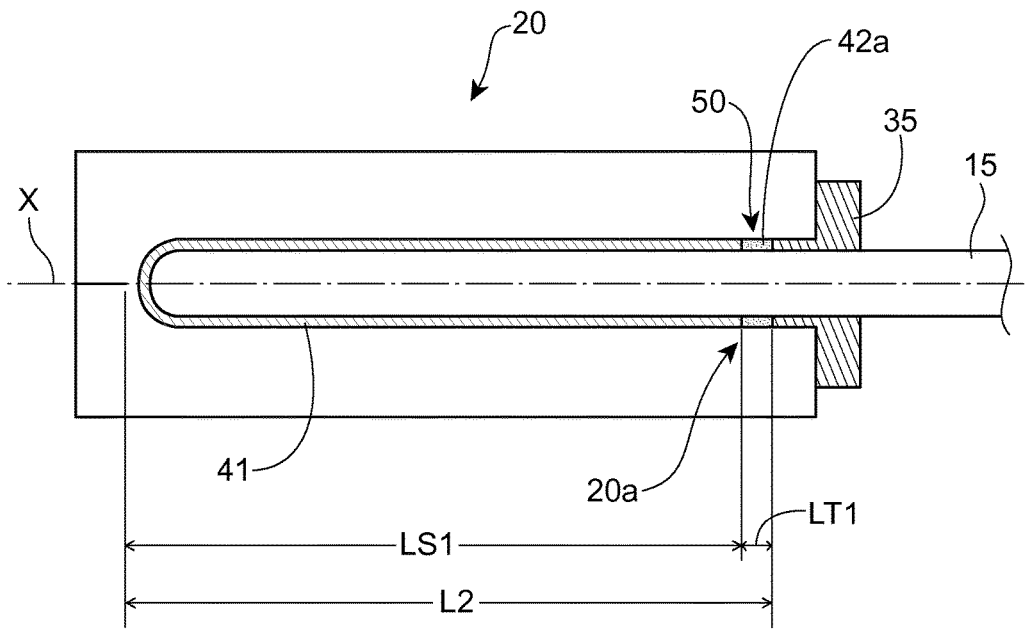
FIG. 9 is a schematic cross-sectional view of another embodiment of the process, showing the second molding station having therein the first component and a molten second material adjacent to the first component's end and comprising the tolerance-elimination element being formed, wherein the latter is configured to compensate for a lengthwise shrinkage of the first plastic material forming the first component. (The injection nozzle is not shown in FIG. 9 for convenience.)

FIG. 9 schematically shows another embodiment of the multi-component housing and the process of the disclosure. A liquid second material 42a is injected into the second mold cavity 20a of the second mold 20 in the location adjacent to the end of the solidified first component 41 made of the first plastic material 41a. (An injection nozzle is not shown for convenience.) The first plastic material 41a has shrunk during solidification so that the solidified first component 41 has a "shrunken" length LS1. Due to the shrinkage of the first plastic material 41a, the length LS1 of the first component 41 is smaller than the length of the first mold cavity 10 that was filled with the liquid first plastic material 41a during a previous process step (not shown). The injected second material 42a fills the second mold cavity 20a, including a space "vacated" by the first plastic material 41a as a result of the shrinkage of the first plastic material 41a, thereby "eliminating" the shrinkage affecting the solidified first plastic component 41.

When the second material 42a solidifies and attaches to the first component 41, the tolerance-elimination element 50 is formed. Due to the significant difference between the length L1 of the liquid first plastic material 41a and a length LT1 (FIG. 9) of the liquid second plastic material 42a forming the tolerance-elimination element 50, the absolute lengthwise shrinkage of the second plastic material 42a forming the tolerance-elimination element 50 is significantly smaller than the absolute lengthwise shrinkage of the first plastic material 41a forming the first component 41. Yet, because the second material 42a "absorbs" the existing lengthwise shrinkage of the first plastic material 41a materialized in the first component 41, and because the absolute lengthwise shrinkage of the intermediate part 45 will now be defined by the absolute shrinkage of the second plastic material 42a forming the tolerance-elimination element 50, the overall absolute lengthwise shrinkage experienced by the intermediate part 45 will also be significantly smaller than the absolute shrinkage experienced by the first component 41.

The length L2 of the second mold cavity 20a is greater than the length of the first mold cavity 10a by a distance that allows for the formation of a desired tolerance-elimination element. This distance can be calculated based on several principal considerations. The difference between the length L2 of the second mold cavity 20a and the length L1 of the first mold cavity 10a should be greater than the expected amount of the shrinkage of the first material 41a. In addition, the difference between the length L2 of the second mold cavity 20a and the length L1 of the first mold cavity 10a should be sufficient for the formation of the tolerance-elimination element 50 having a desired length, particularly its minimal length Hmin in instances where the tolerance-elimination element 50 has an uneven length, as is explained herein.

Depending on the process, materials, and design of the housing being constructed, the minimal length Hmin of the tolerance-elimination element 50 can generally range from 1 mm to about 20 mm, more specifically from about 2 mm to about 15 mm, and even more specifically from about 3 mm to about 10 mm. The maximal length Hmax can range from about 10 mm to about 30 mm and more specifically from about 15 mm to about 25 mm. An average length H of the tolerance-elimination element 50 can range from about 3 mm to about 20 mm and more specifically from about 5 to about 10 mm.

Figure 9A:
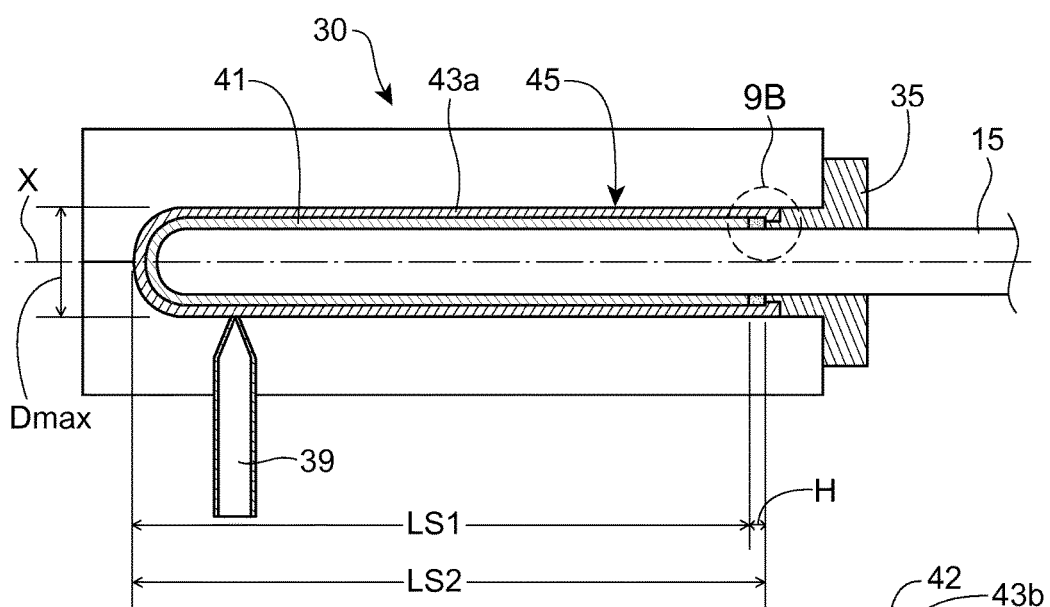
FIG. 9A is a schematic cross-sectional view of the embodiment of the process shown in FIG. 9, and showing the third molding station, wherein the first component and the tolerance-elimination element made of the second material attached to the first component are being overmolded by the third plastic material to form a multi-component housing, wherein the length of the multi-component housing is at least three times greater than the maximal orthogonal dimension of the housing.
Figure 9B:
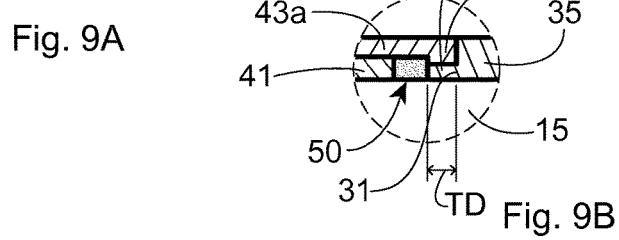
FIG. 9B is an enlarged fragmental view of the cross-section shown in FIG. 9A and showing a the third plastic material completely overmolding the outer surface of the tolerance-elimination element and extending beyond a distant end thereof to at least partially cover a surface of the distal end of the tolerance-elimination element.
Figure 12A:
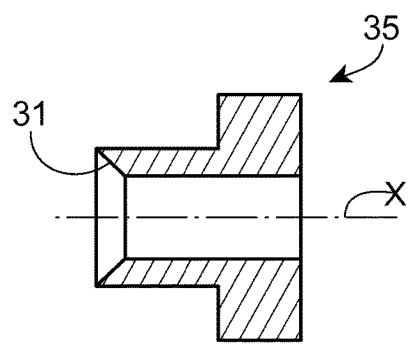
FIG. 12A is a schematic cross-sectional view of yet another exemplary embodiment of a stripper that can be part of the mold tool of the third mold station.
Figure 12B:
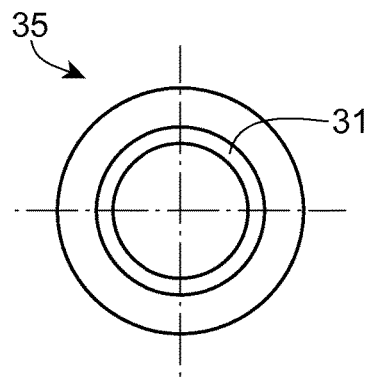
FIG. 12B is a front view of the stripper shown in FIG. 12A.
Figure 13A:
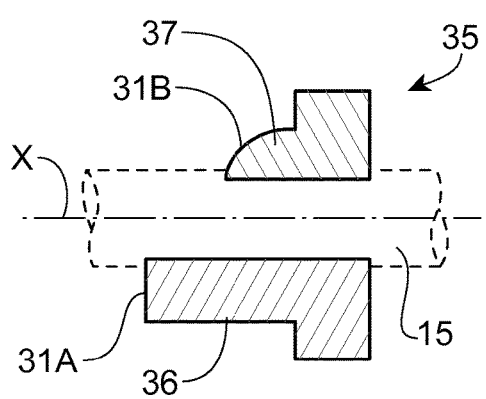
FIG. 13A is a schematic cross-sectional view of an exemplary embodiment of a stripper comprising multiple parts.
Figure 13B:
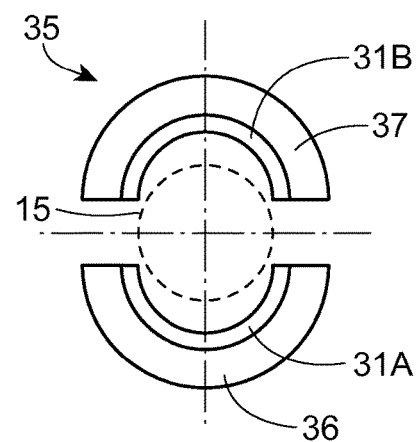
FIG. 13B is a front view of the stripper shown in FIG. 13A.

In the exemplary embodiment of FIG. 9A, the solidified tolerance-elimination element 50 has a constant length H, FIGS. 9C and 9D. Thus, a resulting length LS2 of the intermediate part 45 will be composed by the length LS1 of the solidified first component 41 and the length H of the solidified tolerance-elimination element 50 attached to the end of the first component 41. It should be noted that the length H/Hmax/Hmin of the tolerance-elimination element 50 is measured parallel to the longitudinal axis and from the first component's end that is adjacent to the tolerance-elimination element 50, even though in some embodiments the second material 42a, which forms the tolerance-elimination element 50, can overmold at least a portion of the longitudinally extending surface of the first component 41 adjacent to its end, as is shown in the exemplary embodiment of FIG. 7A.

Therefore, when the intermediate component 45 is being overmolded by a third plastic material 43a in a third mold 30 (FIG. 9A), a manufacturer can rely on a very small lengthwise tolerance for the purposes of this step. This very small lengthwise tolerance is a result of the very small lengthwise shrinkage of the tolerance-elimination element 50—and consequently a very small lengthwise shrinkage of the intermediate portion 45 being overmolded by the third plastic material 43a. The length of the finished multi-component housing is at least three times greater than its maximal orthogonal dimension Hmax.

A third component 43, formed by the solidified third plastic material 43a, may have any suitable wall thickness, which may be constant or alternatively may vary throughout the third component 43. In one exemplary embodiment, particularly suitable for a multi-component housing designed for a toothbrush handle, the third component 43 comprising a TPE material may have a thickness of from about 0.4 mm to about 2.5 mm, and more specifically from about 0.7 mm to about 1.4 mm. The intermediate part 45, likewise, may have any suitable, constant or varying, wall thickness.

In one exemplary embodiment, particularly suitable for a multi-component housing designed for a toothbrush handle, the intermediate component 45 may have a thickness of from about 1.6 mm to about 5.0 mm. The finished housing, comprising at least the first, second, and third plastic materials, may have any suitable wall thickness, which may be either constant or vary. In one exemplary embodiment, particularly suitable for a multi-component housing designed for a toothbrush handle, the multi-component housing may have a combined thickness of from about 2.4 mm to about 7.5 mm, and more specifically from about 2.0 mm to about 3.5 mm, particularly in those parts of the housing that comprise two, three, or more layers of plastic materials.

An enlarged fragmental view of FIG. 9B illustrates an embodiment in which the third plastic material 43a completely overmolds the outer surface of the tolerance-elimination element 50 and extends beyond a distal end 52 of the tolerance-elimination element 50 to at least partially cover the surface of the distal end 52 of the tolerance-elimination element 50. As is pointed out in the context of the embodiment of FIG. 8B, in such instances the third plastic material 43a can form a touch-up distance from about 0.5 mm to about 3 mm beyond the end of the intermediate part 45, thereby beneficially forming a touch-up portion or portions. In the embodiments of FIGS. 7-9A interior walls of the intermediate part 45 are formed mainly by the material of the first component 41, which contacts a portion of the core 15 that is longer than a portion contacted by the second component 42 and/or the third component 43.

FIGS. 14-17 show several exemplary embodiments of the tolerance-elimination element 50 to illustrate that any conceivable shape thereof can be had as long as it is suitable for the design of the multi-component housing 100 being constructed. In the embodiment of FIG. 14, both the proximal end 51 and the distal end 52 of the tolerance-elimination element 50 are straight and inclined relative to the longitudinal axis of the multi-component housing (the latter not shown for convenience). In the embodiment of FIG. 15, the proximal end 51 comprises a concave portion and a straight portion, while the distal end 52 is shaped convexly. In the embodiment of FIG. 16, the proximal end 51 comprises a straight portion disposed between two opposite curved portions, while the distal end 52 is substantially perpendicular to the longitudinal axis. In the embodiment of FIG. 17, the proximal end comprises two straight portions, one of which is perpendicular to the longitudinal axis of the housing and the other is inclined relative thereto, while the distal end 52 is concave. In the embodiment of FIG. 18, each of the proximal end 51 and the distal end 52 comprises a concave shape, wherein portions having maximal length Hmax are disposed opposite to one another, and portions having minimal length Hmin are located on the circumference at about 90 degrees relative to the portions having the maximal length Hmax.

The disclosed process can be successfully utilized for the mass-production of small electronic appliances, such as, e.g., various electric tools and personal-care implements, including toothbrushes, particularly power toothbrushes. In one aspect, a process of the disclosure is directed to making a multi-component housing for a handle of a toothbrush 300, such as, e.g., an exemplary power toothbrush shown in FIG. 22. As is known in the art, a handle of a power tool, such as a power toothbrush, typically serves as a housing for an electric motor, battery, wiring, various electronics, and other driving elements used in such devices. The exemplary power toothbrush 300, shown in FIG. 22, includes a handle 310, comprising a multi-component housing 100 of the disclosure, and a replaceable refill element 320 that includes a movable head 330 having cleaning elements.

Figure 22:
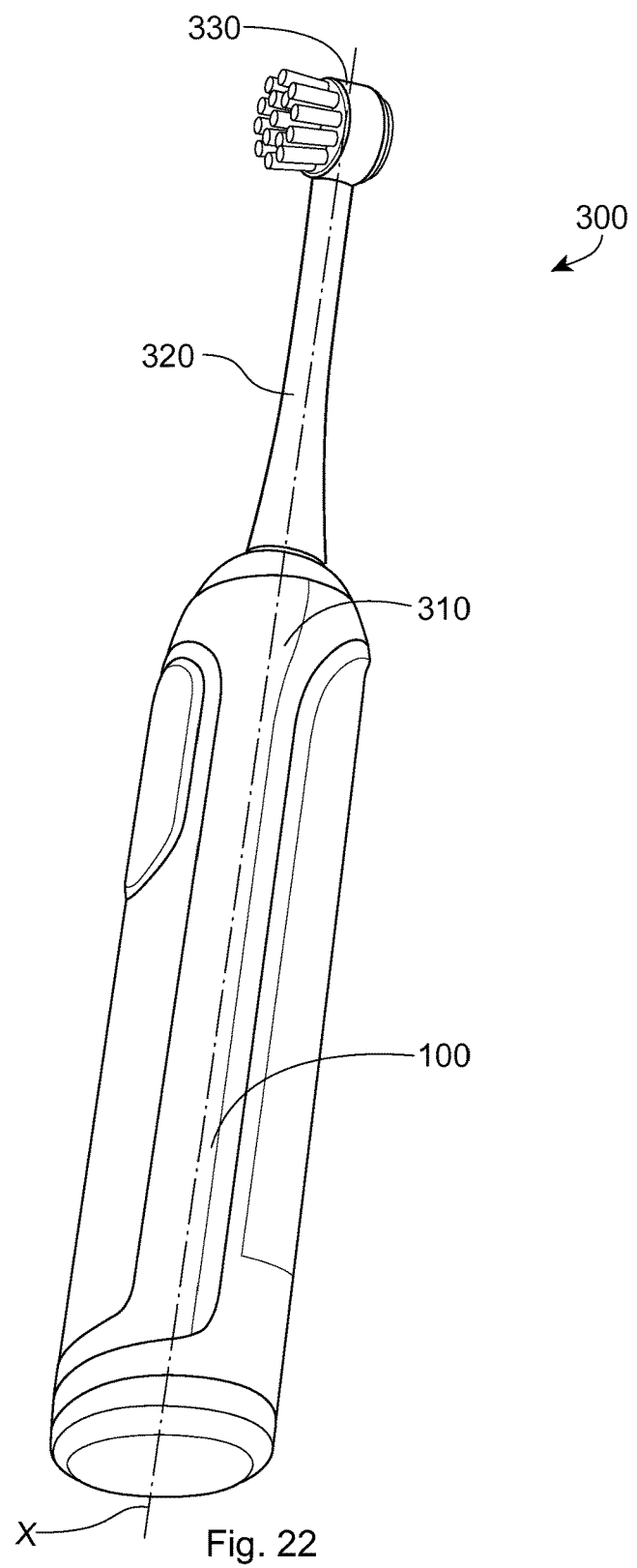
FIG. 22 is a schematic perspective view of an embodiment of a toothbrush having a handle formed by a multi-component housing comprising a tolerance-elimination element.

FIGS. 19-21 show, in perspective or axonometric views, several stages of construction of one specific embodiment of a multi-component housing 100 being made for a handle of a power toothbrush, an exemplary embodiment of which is schematically shown in FIG. 22. FIG. 19 shows a partially made housing comprising a first component 141 made of a first plastic material. FIG. 20 shows an intermediate part 145 comprising the first component 141 attached to a second component 142 made of a second plastic material, wherein the second component 142 includes a tolerance-elimination element 150. FIG. 21 shows a finished housing 100 comprising the intermediate part 145 partially covered with a third component 143 made of a third plastic material, wherein the third plastic material completely overmolds an outside surface of the tolerance-elimination element 150.

The first hard-plastic material 141 and the second hard-plastic material 142 may differ from one another in at least one characteristic selected from the group consisting of color, opacity, porosity, and hardness. In some embodiments, at least one of the first hard-plastic material 141 and the second hard-plastic material 142 can be transparent or translucent, while the soft material can be opaque. In one specific embodiment, the first component 141 can comprise a first hard-plastic material, such as, e.g., a first polypropylene material, the second component 142 can comprise a second hard-plastic material, such as, e.g., a second polypropylene material, and the third component 143 can comprise a soft material, such as, e.g., thermoplastic elastomer. The first component 141 can be transparent or translucent; the second component 142 can be translucent or opaque; and the third component 143 can be opaque.

It should be understood that other plastic materials/components can be utilized in the construction of the multi-component housing, if such materials are required. For example, a fourth and/or fifth and/or sixth plastic material or materials can be used in some embodiments to form additional elements of the housing being made. In the context of a power toothbrush, e.g., a fourth plastic material can be used for sealing control buttons disposed on the toothbrush's handle. The fourth (fifth, sixth, et cetera) plastic material or materials can be identical to at least one of the first, second, and third plastic materials—or alternatively can be different from either one of those.

In the context of mass production, the process of the disclosure, which utilizes the formation of a tolerance-elimination element in a multi-component housing being manufactured, allows manufacturers to rely on very small lengthwise dimension variations of the multi-component housing, and therefore very small lengthwise tolerances, among the individual multi-component housings being produced.

For a great majority of multi-component housings having a nominal overall length of from about 120 mm to about 200 mm and constructed to form, e.g., handles of power toothbrushes or other power tools, the multi-component housings are expected to have a lengthwise tolerance of from 0.01 mm to 0.05 mm in absolute numbers. Assuming that in some instances lengthwise dimension variations among the individual housings may constitute opposite deviations, e.g., +0.05 mm in one housing and −0.05 mm in another, lengthwise maximal dimension variations of the overall lengths among the individual multi-component housings are expected to be not greater than 0.1 mm. In relative terms, the multi-component housings are expected to have a lengthwise tolerance of from about 0.006% to about 0.03% relative to the nominal overall length of the multi-component housing, and lengthwise maximal variations in length of from about 0.012% to about 0.06% among the individual housings.

The dimensions and values disclosed herein are not to be understood as being strictly limited to the exact numerical values recited. Instead, each such dimension is intended to mean both the recited value and a functionally equivalent range surrounding that value, unless otherwise specified. For example, a dimension disclosed as "10 mm" is intended to mean "about 10 mm."

The disclosure of every document cited herein, including that of any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A plurality of mass-produced identical multi-component housings for personal-care implements, each of the housings comprising:
   at least a first component comprising a first plastic material and having a first end and a second end opposite to the first end, a second component comprising a second plastic material, and a third component comprising a third plastic material, the at least first, second, and third components being joined together by molding to form a substantially tubular unitary structure having a longitudinal axis, a top end and a bottom end opposite to the top end, a length L parallel to the longitudinal axis and extending between the top end and the bottom end, and a maximal orthogonal dimension Dmax extending perpendicular to the longitudinal axis, wherein the length L of the housing is at least three times greater than the maximal orthogonal dimension Dmax extending perpendicular to the longitudinal axis;
   wherein each of the housings includes at least one tolerance-elimination element made of the second plastic material and attached to one of the first and second ends of the first component along the longitudinal axis, the tolerance-elimination element having a proximal end and a distal end opposite thereto, the proximal end being adjacent to at least one of the first and second ends of the first component, wherein the tolerance-elimination element has an average length H extending between the proximal end and the distal end parallel to the longitudinal axis, wherein the average length H is at least ten times less than the length L of the housing;
   wherein the third component at least partially forms an outer surface of the housing, so that the tolerance-elimination element is at least partially overmolded by the third plastic material; and
   wherein the tolerance-elimination elements of the plurality of multi-component housings for personal-care implements are structured to cause lengthwise maximal dimension variations of the length L among the individual multi-component housings to be not greater than 0.1 mm.

2. The plurality of mass-produced multi-component housings of claim 1, wherein lengthwise maximal dimensions of the individual multi-component housings differ from one another by not greater than 0.06%.

3. The plurality of mass-produced multi-component housings of claim 1, wherein the tolerance-elimination element of each of the individual housings has a minimal length Hmin of from 1 mm to 20 mm extending parallel to the longitudinal axis.

4. The plurality of mass-produced multi-component housings of claim 1, wherein the tolerance-elimination element of each of the individual housings has a minimal length Hmin of from 2 mm to 15 mm extending parallel to the longitudinal axis.

5. The plurality of mass-produced multi-component housings of claim 1, wherein the tolerance-elimination element of each of the individual housings has a minimal length Hmin of 3 mm to 10 mm extending parallel to the longitudinal axis.

6. The plurality of mass-produced multi-component housings of claim 1, wherein the tolerance-elimination element of each of the individual housings has a maximal length Hmax of from 10 mm to 30 mm, extending parallel to the longitudinal axis.

7. The plurality of mass-produced multi-component housings of claim 1, wherein the tolerance-elimination element of each of the individual housings has an average length of 5 mm to 10 mm extending parallel to the longitudinal axis.

8. The plurality of mass-produced multi-component housings of claim 1, wherein at least one of the first plastic material, the second plastic material, and the third plastic material of each of the individual housings comprises hard-plastic material.

9. The plurality of mass-produces multi-component housings of claim 1, wherein at least one of the first plastic material, the second plastic material, and the third plastic material of each of the individual housings comprises soft plastic.

10. The plurality of mass-produces multi-component housings of claim 1, wherein the tolerance-elimination element of each of the individual housings is made of a hard-plastic material.

11. The plurality of mass-produced multi-component housings of claim 1, wherein the tolerance-elimination element of each of the individual housings is completely overmolded by the third plastic material.

12. The plurality of mass-produced multi-component housings of claim 11, wherein the third plastic material extends beyond the distal end of the tolerance-elimination element in each of the individual housings.

13. The plurality of mass-produced multi-component housings of claim 1, wherein the first plastic material, the second plastic material, and the third plastic material of each of the individual housings differ from one another in at least one characteristic selected from the group consisting of color, opacity, porosity, and hardness.

14. The plurality of mass-produced multi-component housings of claim 1, wherein the tolerance-elimination element of each of the individual housings is integrally attached to the first component.

15. The plurality of mass-produces multi-component housings of claim 1, wherein the average length H varies among at least some of the tolerance-elimination elements by a lengthwise dimension that is at least ten times greater than the lengthwise maximal dimension variations of the length L among the individual multi-component housings.

* * * * *